US006359197B1

(12) United States Patent
Amasino et al.

(10) Patent No.: US 6,359,197 B1
(45) Date of Patent: *Mar. 19, 2002

(54) TRANSGENIC PLANTS WITH ALTERED SENESCENCE CHARACTERISTICS

(75) Inventors: Richard M. Amasino, Madison, WI (US); Susheng Gan, Lexington, KY (US); Yoo-Sun Noh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/971,395

(22) Filed: Nov. 17, 1997

Related U.S. Application Data

(63) Continuation-in-part of application No. 08/413,135, filed on Mar. 29, 1995, now Pat. No. 5,689,042.

(51) Int. Cl.[7] .......................... C12N 15/29; C12N 15/54; C12N 15/82; A01H 5/00
(52) U.S. Cl. ..................... 800/290; 800/278; 800/287; 800/288; 435/69.1; 435/193; 536/23.6; 536/24.1
(58) Field of Search .............................. 536/23.6, 24.1; 800/278, 290, 287, 288, 298; 435/69.1, 193, 320.1, 419, 468

(56) References Cited

U.S. PATENT DOCUMENTS

| 5,177,307 A | 1/1993 | Houck et al. ................ 800/205 |
| 5,268,463 A | 12/1993 | Jefferson ................... 536/23.7 |
| 5,689,042 A | 11/1997 | Amasino et al. ............ 800/205 |

FOREIGN PATENT DOCUMENTS

| EP | 409629 A1 | 1/1991 |
| WO | WO 93/07272 | 4/1993 |
| WO | WO 95/07993 | 3/1995 |
| WO | WO 96/30493 | 10/1996 |

OTHER PUBLICATIONS

Itzhaki et al. Plant Mol. Biol. 22(1): 43–58, Apr. 1993.*
Abstract for NSF Presidential Young Investigator Award No. 8957036 to Amasino, R., May 1993.
H. Itzhaki et al., "An Ethylene–Responsive Enhancer Element is Involved in the Senescence–Related Expression of the Carnation Glutathione–S–Transferase (GSTI) Gene," *Proc. Natl. Acad. Sci. USA*, 91:8925–8929 (1994).
S. Gan et al., "Inhibition of Leaf Senescence by Autoregulated Production of Cytokinin," *Science*, 70: 1986–1988 (1995).
S. Gan et al., "Arabidopsis Thaliana Senescence–Specific Protein (SAG12) Gene, Promoter Region and Complete CDS," EMBL Accession No. U37336, XP–002085506 (Nov. 3, 1995).
Noodén, L. D., "Whole Plant Senescence," in *Senescence and Aging in Plants* (L.D. Noodén and A. C. Leopold, eds), pp. 391–439. Acedemic Press, Inc., San Diego, CA (1988).

Wintermans, J. F. G. M. et al., "Spectrophotometric Characteristics of Chlorophylls a and b and their Pheonphytins in Ethanol," *Biochem. Biophys. Acta.*, 109: 448–453 (1965).
Ainley, W. M. et al., "Regulatable Endogenous Production of Cytokinins Up to 'Toxic' Levels in Transgenic Plants and Plant Tissues," *Plant Mol. Bio.*, 22: 13–23 (1993).
Akiyoshi, D. E. et al., "T–DNA of *Agrobacterium tumefaciens* encodes an enzyme of cytokinin biosynthesis," *Proc. Natl. Acad. Sci. USA*, 81: 5994–5998 (1984).
Bate, N. J. et al., "Expression of Nuclear and Chloroplast Photosynthesis–Specific genes During Leaf Senescence," *J. Exp. Bot.*, 42:801–811 (1991).
Batt, T. et al., "Changing Activities During Senesence and Sites of Synthesis of Photosynthetic Enzymes in Leaves of Labiate, *Preliaa Frutenscens* (L.) Britt," *J. Exp. Bot.*, 26: 569–579 (1975).
Bernhard, W. R. et al., "Differential Expression of Glutamine Synthetase Genes During the Senescence of *Arabidopsis Thaliana* Rosette Leaves," *Plant Science*, 98: 7–14 (1994). No. 1.
Bevan, M. et al., "Structure and transcription of nopaline synthase gene region of the T–DNA," *Nucleic Acids Research*, 11: 369–385 (1983). No. 2.
Blank, A. et al., "Expression of Three Rnase Activities During Natural and Dark–Induced Senescence of Wheat Leaves," *Plant Physiol.*, 97: 1409–1413 (1991).
Chory, J. et al., "A Role for Cytokinins in De–Etiolation in Arabidopsis," *Plant Physiol.*, 104: 339–347 (1994).
Comai, L. et al., "Novel and Useful Properties of a Chimeric Plant Promoter Combining CaMC 35S and MAS Elements," *Plant Mol. Bio.*, 15: 373–381 (1990).
Crespi, M. et al., "Fasciation Induction by the Phytopathogen *Rhodococcus fasciens* Depends Upon a Linear Plasmid Encoding a Cytokinin Synthase Gene," *Embo. J.*, 11: 795–804 (1992). No. 3.
Crowell, D. N. et al., "Cytokinin–Induced mRNAs in Cultured Soybean Cells," *Proc. Natl. Acad. Sci. USA*, 87: 8815–8819 (1990).
De Bellis, L. et al., "Glyoxylate Cycle Enzymes in Peroxisomes Isolated from Petals of Pumpkin (Cucurbita sp.) During Senescence," *Plant Cell Physiol.*, 32(8)–1227–1235 (1991).
Friedrich, J. W. et al., "Photosynthesis, Leaf Resistances, and Ribulose–1, 5–Bisphosphate Carboxylase Degradation in Senescing Barley Leaves," *Plant Physiol.*, 65: 1103–1107 (1980).

(List continued on next page.)

Primary Examiner—David T. Fox
(74) Attorney, Agent, or Firm—Mueting, Raasch & Gebhardt, P.A.

(57) ABSTRACT

The identification of senescence-specific promoters from plants is described. Using information from the first senescence-specific promoter, SAG12 from Arabidopsis, other homologous promoters from another plant have been identified. Such promoters may be used to delay senescence in commercially important plants.

7 Claims, 3 Drawing Sheets

OTHER PUBLICATIONS

Goldberg, S. B. et al., "Nucleotide Sequence of the tmr Locus of *Agrobacterium tumefaciens* pTi T37 T–DNA," *Nucleic Acids Res.*, 12: 4665–4677 (1984). No. 11.

Graham. I. A. et al., "Induction of Malate Synthase Gene Expression in Senescent and Detached Organs of Cucumber," *Plant Cell*, 4: 349–357 (1992).

Heidekamp, F. et al., "Nucleotide Sequence of the *Agrobacterium tumefaciens* Octopine Ti Plasmid–Encoded tmr Gene," *Nucleic Acids Res.*, 11: 6211–6223 (1983). No. 18.

Hensel, L. L. et al., "Developmental and Age–Related Processes That Influence the Longevity and Sensescence of Photosynthetic Tissues in Arabidopsis," *The Plant Cell*, 5: 553–564 (1993).

Horsch, R. B. et al., "A simple and general method for transferring genes into plants," *Science*, 227: 1229–1231 (1985).

Jiang, C. Z. et al., "Photosynthesis, Rubisco Activity and Amount, and their Regulation by Transcription in Senescing Soybean Leaves," *Plant Physiol.*, 101: 105–112 (1993).

John, M. C. et al., "Expression of an Agrobacterium–Ti Plasmid gene Involved in Cytokinin Biosynthesis is Regulated by Virulence Loci and Induced by Plant Phenolic Compounds," *J. Bacteriol.*, 170: 790–795 (1988). No. 2.

Kamachi, K. et al., "Changes in Cytosolic Glutamine Synthetase Polypeptide and Its Messenger RNA in a Leaf blade of Rice Plants During Natural Senescence," *Plant Physiol.*, 98: 1323–1329 (1992).

Larson, E. et al., "Artificial Reductant Enhancement of the Lowry Method for Protein Determination," *Anal. Biochem.*, 155: 243–248 (1986).

Lewin, R., "When Does Homology Mean Something Else?," *Science*, 237: 1570 (1987).

Li, Y. et al., "Altered Morphology in Transgenic Tobacco Plants That Overproduced Cytokinins in Specific Tissues and Organs," *Dev. Biol.*, 153: 386–395 (1992).

Lohman, K. L. et al., "Molecular Analysis of Natural Leaf Senescence in *Arabidposis Thaliana*,"*Phys. Plantarum*, 92: 322–328 (1994).

Lowry, O. H. et al. "Protein Measurement with the Folin Phenol Reagent," *J. Biol Chem.*, 193: 265–275 (1951).

Martineau, B. et al., "Fruit–Specific Expression of the *A. Tumefaciens* Isopentenyl Transferase Gene in Tomato: Effects on Fruit Ripening and Defense–Related Gene Expression in Leaves," *The Plant Journal*, 5(1): 11–19 (1994).

Medford, J. I. et al., "Alterations of Endogenous Cytokinins in Transgenic Plants Using a Chimeric Isopentenyl Transferase Gene," *The Plant Cell*, 1: 403–413 (1989).

Noodén, L. D. et al., "Correlation of xylem sap cytokinin levels with monocarpic senescence in soybean," *Plant Physiol.*, 93: 33–39 (1990).

Ooms, G. et al., "Phenotypic Changes in T–Cyt–Transformed Potato Plants Are Consistent with Enhanced Sensitivity of Specific Cell Types to Normal Regulation by Root–Derived Cytokinin," *Plant Mol. Bio.*, 17: 727–743 (1991).

Peterson, G. L. "A Simplification of the Protein Assay Method of Lowry et al. Which is More Generally Acceptable," *Anal. Biochem.*, 83: 346–356 (1977).

Pistelli, L. et al. "Effect of Leaf Senescence on Glycoxylate Cycle Enzyme Activities," *Aust. J. Plant Physiol.*, 19: 723–729 (1992).

Puissant, C. et al., "An Improvement of the Single–Step Method of RNA Isolation by Acid Guanidinium Thiocyanate–Phenol–Chloroform Extraction," *BioTechniques*, 8: 148–149 (1990). No. 2.

Reeck, G. R. et al., "Homology" in Proteins and Nucleic Acids: A Terminology Muddle and a Way Out of It, *Cell*, 50: 667 (1987).

Sambrook, J. et al., "*Molecular Cloning: A Laboratory Manual*," Cold Spring Harbor Laboratory Press, Cold Spring Harbor Press, NY (1989), 2nd Edition, pp. v–xxv.

Smart, C. M. et al., "Delayed Leaf Senescence in Tobacco Plants Transformed with tmr, a Gene for Cytokinin Production in Agrobacterium," *The Plant Cell*, 3: 647–656 (Jul. 1991).

Smigocki, A. C. et al., "Cytokinin Content and Tissue Distribution in Plants Transformed by a Reconstructed Isopentenyl Transferase Gene," *Plant Mol. Bio.*, 16: 105–115 (1991).

Somerville, C. R. et al., "Isolation of Photorespiration Mutants in *Arabidopsis Thaliana*," in *Methods of Chloroplast Molecular Biology*, (M. Edelman et al., eds.), pp. 129–137. Elsevier Biomedical Press, New York, NY (1982).

Strabala, T. J. et al., "Isolation and Characterization of an ipt Gene from the Ti Plasmid Bo542," *Mol. Gen. Genet.*, 216: 388–394 (1989).

Taylor, C. B. et al., "RNS2—A Senescence–Associated Rnase of Arabidopsis that Diverged from the S–RNases Before Speciation," *Proc. Natl. Acad. Sci. USA*, 90: 5118–5122 (1993).

Thomas, H. et al., "Leaf Senescence," *Ann. Rev. Plant Physiol.*, 31: 83–111 (1980).

Thomson, W. W. et al., "Ultrastructure and Senescence in Plants," in *Plant Senescence: Its Biochemistry and Physiology* (W.W. Thomsen et al., eds.) pp. 20–30. American Society of Plant Physiologists, Rockville, MD (1987).

Valvekens, D. et al., "*Agrobacterium tumefaciens*mediated transformation of Arabidopsis root explants using kanamycin selection," *Proc. Natl. Acad. Sci. USA*, 85: 5536–5540 (1988).

Van Loven, K. et al., "Morphometric Analysis of the Growth of Phsp70–ipt Transgenic Tobacco Plants," *J. Exp. Botany*, 44(268): 1671–1678 (Nov. 1993).

Van Staden, J. et al., "Cytokinins and Senescence," Chapter 9 in *Senescence and Aging in Plants*, Academic Press, Inc. (1988).

Woolhouse, H. W., "The Biochemistry and Regulation of Senescence in Chloroplasts," *Can. J. Bot.*, 62: 2934–2942 (1984).

\* cited by examiner

▼a -2073 bp EcoR V
GATATCTCTT TTTATATTCA AACAATAAGT TGAGATATGT TTGAGAAGAG GACAACTATT
CTCGTGGAGC ACCGAGTCTG TTTTATATTA GAAACCCGAT TGTTATTTTT AGACTGAGAC
AAAAAAGTAA AATCGTTGAT TGTTAAAATT TAAAATTAGT TTCATCACGT TTCGATAAAA
AAATGATTAG TTATCATAGC TAATATAGCA TGATTCTAAA TTTGTTTTTT GACACCCTTT
TTTTCTCTCT TTGGTGTTTT CTTAACATTA GAAGAACCCA TAACAATGTA CGTTCAAATT
AATTAAAAAC AATATTTCCA AGTTTTATAT ACGAAACTTG TTTTTTTAAT GAAAACAGTT
GAATAGTTGA TTATGAATTA GTTAGATCAA TACTCAATAT ATGATCAATG ATGTATATAT
ATGAACTCAG TTGTTATACA AGAAATGAAA ATGCTATTTA AATACCGATC ATGAAGTGTT
AAAAAGTGTC AGAATATGAC ATGAAGCGTT TTGTCCTACC GGGTATCGAG TTATAGGTTT
GGATCTCTCA AGAATATTTT GGGCCATATT AGTTATATTT GGGCTTAAGC GTTTTGCAAA
GAGACGAGGA AGAAAGATTG GGTCAAGTTA ACAAAACAGA GACACTCGTA TTAGTTGGTA
CTTTGGTAGC AAGTCGATTT ATTTGCCAGT AAAAACTTGG TACACAACTG ACAACTCGTA
TCGTTATTAG TTTGTACTTG GTACCTTTGG TTAAGAAAAA GTTGATATAG TTAAATCAGT
TGTGTTCATG AGGTGATTGT GATTTAATTT GTTGACTAGG GCGATTCCTT CACATCACAA
TAACAAAGTT TTATAGATTT TTTTTTATAA CATTTTTGCC ACGCTTCGTA AAGTTTGGTA
TTTACACCGC ATTTTTCCCT GTACAAGAAT TCATATATTA TTTATTTATA TACTCCAGTT
GACAATTATA AGTTTATAAC GTTTTTACAA TTATTTAAAT ACCATGTGAA GATCCAAGAA
TATGTCTTAC TTCTTCTTTG TGTAAGAAAA CTAACTATAT CACTATAATA AAATAATTCT
AATCATTATA TTTGTAAATA TGCAGTTATT TGTCAATTTT GAATTTAGTA TTTTAGACGG
TTATCACTTC AGCCAAATAT GATTTGGATT TAAGTCCAAA ATGCAATTTC GTACGTATCC
CTCTTGTCGT CTAATGATTA TTTCAATATT TCTTATATTA TCCCTAACTA CAGAGCTACA
TTTATATTGT ATTCTAATGA CAGGGAAACT TTCATAGAGA TTCAGATAGA TGAAATTGGT
GGGAAACATC ATTGAACAGG AAACTTTTAG CAAATCATAT CGATTTATCT ACAAAAGAAT
ACTTAGCGTA ATGAAGTTCA CTTGTTGTGA ATGACTATGA TTTGATCAAA TTAGTTAATT
▼b -602 bp Hind III
TTGTCGAATC ATTTTTCTTT TTGATTTGAT TAAGCTTTTA ACTTGCACGA ATGGTTCTCT
TGTGAATAAA CAGAATCTTT GAATTCAAAC TATTTGATTA GTGAAAAGAC AAAAGAAGAT
TCCTTGTTTT TATGTGATTA GTGATTTTGA TGCATGAAAG GTACCTACGT ACTACAAGAA
AAATAAACAT GTACGTAACT ACGTATCAGC ATGTAAAAGT ATTTTTTTCC AAATAATTTA
TACTCATGAT AGATTTTTTT TTTTTGAAAT GTCAATTAAA AATGCTTTCT TAAATATTAA
TTTTAATTAA TTAAATAAGG AAATATATTT ATGCAAAACA TCATCAACAC ATATCCAACT
TCGAAAATCT CTATAGTACA CAAGTAGAGA AAATAAATTT TACTAGATAC AAACTTCCTA
ATCATCAATT ATAAATGTTT ACAAAACTAA TTAAACCCAC CACTAAAATT AACTAAAAAT
CCGAGCAAAG TGAGTGAACA AGACTTGATT TCAGGTTGAT GTAGGACTAA AATGGCTACG
TATCAAACAT CAACGATCAT TTAGTTATGT ATGAATGAAT GTAGTCATTA CTTGTAAAAC
                                           -1 ▼+1
AAAAATGCTT TGATTTGGAT CAATCACTTC ATGTGAACAT TAGCAATTAC ATCAACCTTA
TTTTCACTAT AAAACCCCAT CTCAGTACCC TTCTGAAGTA ATCAAATTAA GAGCAAAAGT
            ▼Nco I --->IPT
CATTTAACTT TCCTAAAACC ATGGACCCTG CATCTAATTT TCGGTCCAAC TTGCACAGGA
AAGACGACGA CCGCGATAGC TCTTGCCCAG CAGACAGGGC TTCCAGTCCT TTCGCTTGAT
CGGGTCCAAT GCTGTCCTCA ACTATCAACC GGAAGCGGAC GACCAACAGT GGAAGAACTG
AAAGGAACGA CGCGTCTCTA CCTTGATGAT CGGCCTCTGG TGGAGGGTAT CATCGCAGCC
AAGCAAGCTC ATCATAGGCT GATCGAGGAG GTGTATAATC ATGAGGCCAA CGGCGGGCTT
ATTCTTGAGG GAGGATCCAC CTCGTTGCTC AACTGCATGG CGCGAAACAG CTATTGGAGT
GCAGATTTTC GTTGGCATAT TATTCGCCAC AAGTTACCCG ACCAAGAGAC CTTCATGAAA
GCGGCCAAGG CCAGAGTTAA GCAGATGTTG CACCCCGCTG CAGGCCATTC TATTATTCAA
GAGTTGGTTT ATCTTTGGAA TGAACCTCGG CTGAGGCCCA TTCTGAAAGA GATCGATGGA
TATCGATATG CCATGTTGTT TGCTAGCCAG AACCAGATCA CGGCAGATAT GCTATTGCAG
CTTGACGCAA ATATGGAAGG TAAGTTGATT AATGGGATCG CTCAGGAGTA TTTCATCCAT
GCGCGCCAAC AGGAACAGAA ATTCCCCCAA GTTAACGCAG CCGCTTTCGA CGGATTCGAA
                                 ▼Sst I --->NOS-ter
GGTCATCCGT TCGGAATGTA TTAGGTTACG CCAGCCCTGA GCTCGATCGT TCAAACATTT
GGCAATAAAG TTTCTTAAGA TTGAATCCTG TTGCCGGTCT TGCATGATT ATCATATAAT
TTCTGTTGAA TTACGTTAAG CATGTAATAA TTAACATGTA ATGCATGACG TTATTTATGA
GATGGGTTTT TATGATTAGA GTCCCGCAAT TATACATTTA ATACGCGATA GAAAACAAAA
TATGGCGCGC AAACTGGGAT AAATTATCGC GCGCGGTGTC ATCTATGTTA CTAGATCGAA
TTC

FIG. 3

TRANSGENIC PLANTS WITH ALTERED SENESCENCE CHARACTERISTICS

CROSS-REFERENCE TO RELATED APPLICATIONS

This application is a continuation-in-part of U.S. patent application Ser. No. 08/413,135 filed Mar. 29, 1995, now U.S. Pat. No. 5,689,042.

STATEMENT REGARDING FEDERALLY SPONSORED RESEARCH OR DEVELOPMENT

This invention was made with United States government support awarded by the following agencies: DOE Grant Nos. DE-FG-02-97ER20280 and DE-FC05-92OR22072; USDA AGRICCREE Grant No. 95-37100-1614; and NSF Grant Nos. IBN-9318481 and IBN-9723809. The United States may have certain rights in this invention.

BACKGROUND OF THE INVENTION

In general, the present invention relates to the field of plant molecular biology. Specifically, the present invention relates to transgenic plants with inserted transgenes that are activated by development-specific promoters.

Leaf senescence is a phase of development during which cells undergo distinct metabolic and structural changes prior to cell death (Noodén, *Senescence and Aging in Plants,* (L. D. Noodén and A. C. Leopold, Ed.), pp. 391–439, Academic Press, San Diego, Calif., 1988). It is an important phase in the plant life cycle that is thought to contribute to fitness by recycling nutrients to actively growing regions. The initiation of leaf senescence can be induced by a variety of external factors such as shading, mineral deficiency, drought and pathogen infection (Thomas, et al., *Ann. Rev. Plant Physiol.* 31:83–111, 1980) and by developmental processes such as seed development (Noodén, 1988, supra). In the absence of such factors, leaf senescence occurs in an age-dependent manner in many species (Batt, et al., *J. Exp. Bot.* 26:569–579, 1975; Hensel, et al., *Plant Cell* 5:553–564, 1993; Jiang, et al., *Plant Physiol.* 101:105–112, 1993).

Physiological and genetic studies indicate that senescence is a highly regulated process (Noodén, 1988, supra; Thomas, 1980, supra). The progression of a leaf through the senescence program is visibly marked by the loss of chlorophyll and consequent yellowing, a result of the disassembly of the chloroplast (Thomson, et al., *Plant Senescence: Its Biochemistry and Physiology,* pp. 20–30, 1987; Woolhouse, *Can. J. Bot.* 62:2934–2942, 1984). Leaf senescence involves degradation of proteins, nucleic acids and membranes, and the subsequent transport of the nutrients resulting from this degradation to other regions of the plant, such as developing seeds, leaves, or storage organs (Noodén, 1988, supra; Woolhouse, 1984, supra).

Molecular studies indicate that changes in gene expression are associated with the senescence program. The levels of mRNAs encoding proteins involved in photosynthesis decrease during senescence (Bate, et al., *J. Exp. Bot.* 42:801–811, 1991; Hensel, et al., *Plant Cell* 5:553–564, 1993; Jiang, et al., *Plant Physiol.* 101:105–112, 1993), while mRNA levels of genes encoding proteins thought to be involved in the senescence program increase (Graham, et al., *Plant Cell* 4:349–357, 1992, Hensel, et al., *Plant Cell* 5:553–564, 1993; Kamachi, et al., *Plant Physiol.* 93:1323–1329, 1992; Taylor, et al., *Proc. Natl. Acad. Sci. USA* 90:5118–5122, 1993). The activities of several enzymes that are likely to play a role in the breakdown and mobilization of nutrients have also been shown to increase during senescence (Blank, et al., *Plant Physiol.* 97:1409–1413, 1991; Debellis, et al., *Plant Cell Physiol.* 32:1227–1235, 1991; Friedrich, et al., *Plant Physiol.* 65:1103–1107, 1980; Pistelli, et al., *J. Plant Physiol.* 19:723–729, 1992).

Although the general changes that occur during senescence are known, many of the biochemical details of how nutrient remobilization occurs remain to be determined. Furthermore, little is understood of how the changes in gene expression that accompany senescence are regulated.

Promoters capable of promoting gene expression during the plant developmental stage of senescence are needed in the art of plant molecular biology.

As a first step towards obtaining this goal, we investigated macromolecular changes that occur during leaf senescence in *Arabidopsis thaliana.* The onset of leaf senescence in Arabidopsis is determined by leaf age (Hensel, et al., supra). This predictability of the senescence program in Arabidopsis facilitated an integrated study of changes in RNA, chlorophyll, protein, and gene expression associated with natural leaf senescence in the intact plant. We also used this system, as recited here, to isolate and characterize the temporal expression patterns of mRNAs that increase and decrease in abundance during leaf senescence. These senescence-specific mRNAs allowed us, as described below, to isolate and characterize novel senescence-specific promoters.

BRIEF SUMMARY OF THE INVENTION

The present invention is a genetic construct comprising an SAG12 promoter sequence operably connected to a protein-coding DNA sequence not natively connected to the promoter sequence. Preferably, the SAG12 promoter sequence is the SAG12-1 sequence. Most preferably, the SAG12 promoter is the first 602 bp of SEQ ID NO:2 and the protein-coding DNA sequence encodes isopentenyl transferase.

The present invention is also a cell or a plant containing the genetic construct.

It is an object of the present invention to provide a genetic construct with a promoter sequence enabling senescence-specific gene expression operably linked to a protein-coding sequence.

It is another object of the present invention to provide a senescence-specific promoter linked to a sequence encoding an enzyme that catalyzes the synthesis of a plant hormone, preferably cytokinin.

It is another object of the present invention to provide a senescence-specific promoter linked to an isopentenyl transferase sequence.

It is another object of the present invention to provide a transgenic plant that contains a transgene expressed only in senescing tissue.

It is a feature of the present invention that gene expression can be targeted specifically to senescing tissue, thus avoiding constitutive expression that could be damaging.

Other objects, advantages, and features of the present invention will become apparent after review of the specification, drawings, and claims.

BRIEF DESCRIPTION OF THE SEVERAL VIEWS OF THE DRAWINGS

FIG. 3 is the nucleotide sequence of SAG12-1 promoter/IPT/NOS-ter construct. The "a" and "b" labels correspond to "a" and "b" in FIGS. 1 and 2.

DETAILED DESCRIPTION OF THE INVENTION

Figure 1:
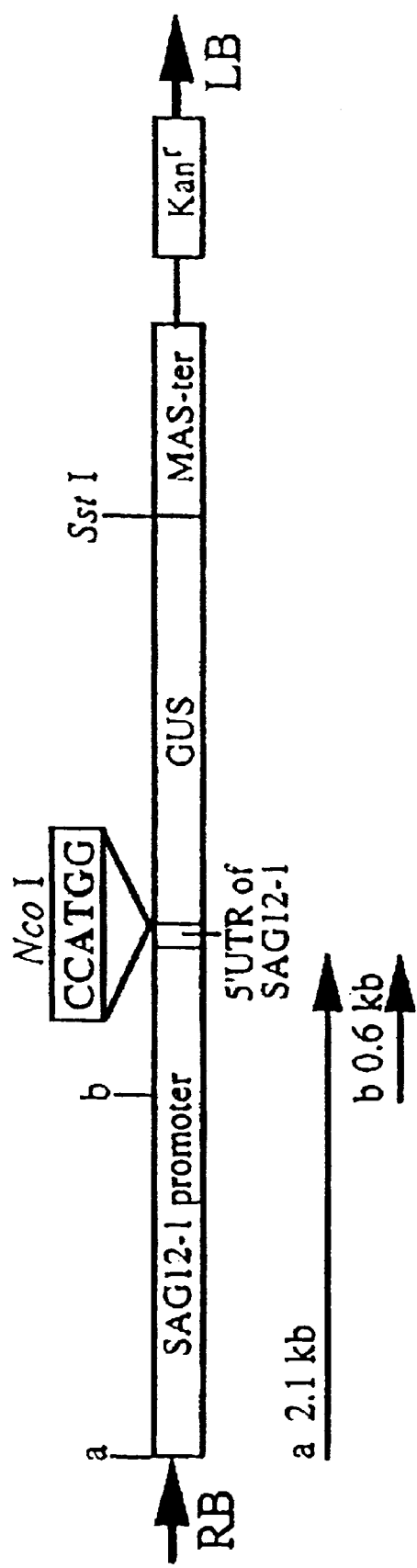
FIG. 1 is a schematic map of SAG12-1 promoter/GUS/MAS-ter construct in a binary vector.

One aspect of the present invention is a genetic construct comprising a senescence-specific promoter operably linked to a foreign gene sequence that is not natively associated with the promoter. An exemplary useful senescence-specific promoter, identified here as the SAG12 promoter, has been characterized. The original SAG12 promoter was identified in Arabidopsis. Subsequent work in Brassica has demonstrate that promoters of similar function can be found in other plants as well. The availability of a senescence-specific promoter has also enabled the creation of transgenic plants with altered senescence morphology e.g. delayed senescence. This finding offers a mechanism to extend the growth of useful plants.

Isolation of a first SAG12 promoter from *Arabidopsis thaliana*, SAG12-1, is described in detail below. Basically, a senescence-specific cDNA, here called "SAG12", was isolated along with the genomic clone corresponding to the SAG12 cDNA. The SAG12-1 promoter was isolated from upstream genomic material. The term "SAG" designates a senescence associated gene.

SEQ ID NO:1 and FIG. 3 contain a nucleotide sequence for one embodiment of the SAG12-1 promoter. SEQ ID NO:2 describes a truncated version of this promoter. Both versions of the SAG12-1 promoter are sufficient to promote gene expression in a senescence-specific manner.

Also described below is a second senescence-specific promoter, isolated from Arabidopsis in a similar manner. The second promoter is here designated "SAG13." The SAG13 promoter was also isolated from the Arabidopsis genome. SEQ ID NO:3 contains the nucleotide sequence for the SAG13 promoter, including 1782 base pairs upstream of the transcription start site.

In addition, two SAG12 promoters from *Brassica napus*, a tetraploid plant species, have been isolated and characterized as described below. These promoters were isolated using information from Arabidopsis SAG promoters. These promoters are designated BnSAG12-1 and BnSAG12-2. The nucleotide sequences of BnSAG12-1 and BnSAG12-2 are provided in SEQ ID NO:4 and SEQ ID NO:5, respectively.

By "senescence-specific promoter" and "senescence associated promoter" it is meant to indicate that the SAG12-1, SAG13, and BnSAG12 promoters are capable of preferentially promoting gene expression in a plant tissue in a developmentally regulated manner such that expression of a 3' protein coding region occurs substantially only when the plant tissue is undergoing senescence. The term is intended to encompass these particular promoters as well as analogous promoters isolated from other plant species which have similar expression characteristics.

The Arabidopsis SAG12 promoter includes nucleotides sufficiently homologous to the first 602 bp of SEQ ID NO:2 so that the promoter is capable of expressing genes preferably in a senescing tissue. Also, the senescence-specific promoter can consist of the nucleotide sequence of SEQ ID NO:2.

Preferably the SAG13 promoter includes a portion of the sequence set forth in SEQ ID NO:3 below. While this entire sequence is sufficient for senescence-specific promoter activity, it is also likely that a smaller sequence will also be sufficient. The bounds of such a smaller sequence can readily be determined by truncation of the sequence of SEQ ID NO:3 below, followed by empirical testing of such truncations for senescence specific promoter activity.

The Examples below describe the isolation of the initial senescence-specific cDNA clones from Arabidopsis. These Arabidopsis cDNA clones were used to identify four senescence-specific genomic DNA clones from Arabidopsis and Brassica, which are designated SAG12-1, SAG13, BnSAG12-1, and BnSAG12-2. The characterization of these clones is detailed in the examples below. It is believed that there are other senescence-specific promoters with sufficient homology to SAG12-1, SAG13, BnSAG12-1, or BnSAG12-2 that can be isolated by these same techniques and would be suitable for use in the present invention. One could easily use the techniques described below to obtain these homologous promoters.

Creation of an SAG12 Promoter

In the Examples below, described is the isolation of the SAG12 promoter using the SAG12 cDNA clone. This cDNA clone was obtained from an RNA molecule that appears to be expressed only during senescence.

The SAG12 cDNA has been used to screen an Arabidopsis library to obtain the SAG12 gene. The gene was originally designated SAG12-1 in the belief that there were two SAG12 genes in Arabidopsis, although it is now believed that there is only one. The SAG12-1 promoter was obtained from the SAG12-1 genomic clone. SEQ ID NO:1 and FIG. 3 disclose the sequence of 2073 bp of the SAG12-1 promoter. Further studies, also described below, showed that the SAG12-1 promoter could be truncated to 602 bp and still remain functional. SEQ ID NO:2 describes the 602 bp linked to a 5' untranslated region of the SAG12-1 gene.

To obtain a SAG12 promoter, one could follow one of several paths. Most easily, one could create an oligonucleotide probe from the sequences disclosed in SEQ ID NOs:1 and 2 or FIG. 3 and probe a genomic library of Arabidopsis, Brassica, or another plant species to recover a copy of the SAG12 promoter. One useful probe for the identification of SAG genes from diverse species of plants is a sequence that is highly conserved among known SAG12 promoters corresponding to bp 1291–1603 of SEQ ID NO:1, bp 1272–1585 of SEQ ID NO 4, or bp 2202–2517 of SEQ ID NO:5. SEQ ID NO:1, SEQ ID NO:4, and SEQ ID NO:5 correspond to a SAG12 promoter from Arabidopsis and two SAG12 promoters from Brassica, respectively. This level of conservation indicates a correlation to senescence-specific promoter activity. Thus, the high degree of conservation of this sequence, it is expected that DNA fragments from other plant species including a sequence that is at least about 75% homologous to bp 1291–1603 of SEQ ID NO:1, bp 1272–1585 of SEQ ID NO:4, or bp 2202–2517 of SEQ ID NO:5 would promote senescence-specific expression in plants.

It is envisioned that minor nucleotide additions, deletions, and mutations will not affect the function of the SAG12-1 promoter. Furthermore, it is possible, if not likely, that there may be variations in sequence of the SAG12 gene (or SAG13) and promoter among populations of Arabidopsis stocks because of normal allelic variations. Furthermore, it is likely and anticipated that homologous sequences can be recovered from other plants. Therefore, the sequence of a suitable SAG promoter might not be identical to that disclosed in SEQ ID NOs:1 or 2. Detailed below is an assay by which one may determine whether a candidate genomic sequence is sufficiently homologous to the senescence-specific SAG12-1 promoter to be suitable for the present invention.

Additionally, it is envisioned that the 602 bp of SEQ ID NO:1 may be further truncated and still produce a suitable SAG12 promoter. One of ordinary skill in this technology can readily appreciate that 5' or 3' truncations, or internal deletions, from this 602 bp sequence can be made, and those truncations empirically tested for senescence-specific activity, to find such smaller truncations of the SAG12-1 promoter.

Preferably, a portion of the 5' untranslated region of the SAG12-1 gene will be added to the promoter sequence. SEQ ID NOs:1 and 2 disclose this sequence. In FIG. 3, the 5' untranslated region is the region between the +1 symbol and the "Nco I" symbol.

Creation of SAG13 Promoter

A similar method was used to isolate and identify the SAG13 promoter set forth in the Examples below. Variations in SAG13 sequence, due to allelic variations and the like, are expected as well. SAG12 and SAG13 are not notably homologous.

Assay of a Candidate Promoter

Once a candidate genomic sequence has been isolated, one may wish to determine whether or not this DNA sequence is a SAG12 or a SAG13 promoter. One could determine the DNA sequence of a putative promoter using techniques familiar to one of ordinary skill in the art of plant molecular biology. If the candidate sequence is identical or homologous to a portion of the first 2073 bp of SEQ ID NO:1, the first 602 bp of SEQ ID NO:2, or the first 1782 bp of SEQ ID NO:3, then the sequence is a suitable SAG12 or SAG13 promoter. Another category of suitable SAG12 promoter would have at least about 75% DNA sequence homology with bp 1291–1603 of SEQ ID NO:1, bp 1272–1585 of SEQ ID NO:4, or bp 2202–2517 of SEQ ID NO:5, and would also exhibit senescence-specific promoter activity.

If the putative senescence-specific promoter is not identical, however, and is closely homologous, i.e. at least about 75% homologous, one may have isolated a copy of an allelic SAG12 or SAG13 promoter. One would wish to do a functional assay to determine whether or not this sequence was sufficiently homologous to the first 602 bp of SEQ ID NO:2, the first 2073 bp of SEQ ID NO: 1, or the first 1782 bp of SEQ ID NO:3 to be suitable for the present invention.

By "sufficiently homologous" it is meant that a candidate promoter natively conditions the expression of a gene sufficiently homologous in nucleotide sequence to one of the known SAG12 genes such that the SAG12 DNA or cDNA will hybridize to nucleotides (DNA, RNA or cDNA) made by the candidate gene. An assay for determining whether a candidate sequence is senescence-specific is appropriate and such an assay is described below.

To make this determination, one could follow the examples described below and attach the candidate promoter to a reporter protein coding sequence, such as the GUS sequence encoding the enzyme beta-glucuronidase. The sequence of the GUS gene is described in U.S. Pat. No. 5,268,463. Transformation of a plant with an expression cassette including the GUS sequence allows one to determine whether or not the GUS reporter sequence was expressed in only the senescing tissues, was constitutively expressed, or was not expressed at all. Only a result indicating that the reporter sequence is only expressed in senescing tissues and not other tissues would indicate a suitable promoter.

Alternatively, the candidate sequence could be attached to the isopentenyl transferase sequence and transformed into tobacco plants, as we have described below. Table 2 of the Examples discloses specific differences between plants transformed with the SAG12 promoter linked to an IPT gene and transgenic control plants containing a construct with the SAG12 promoter linked to the GUS reporter gene. A candidate promoter would have to perform equivalently to be suitable for the present invention.

Therefore, other candidate promoters may be identified using these criteria. It may be isolatable or hybridizable with an oligonucleotide probe created from the first 2073 bp or SEQ ID NO:1, the first 602 bp of SEQ ID NO:2, or a corresponding region of SEQ ID NO:3 or SEQ ID NO:4 or 5. Second, it must promote senescence-specific expression of a reporter gene, such as GUS. Third, it must provide equivalent senescence-specific expression as the SAG12 or SAG13 promoter described in Table 2 of the Examples.

Creation of Genetic Construct

Once one has obtained an SAG12 or SAG13 promoter, a genetic construct must be created containing both that promoter and a protein-coding sequence. By "genetic construct" it is meant to describe an operably connected promoter and gene sequence. Typically the promoter sequence is 5' or "upstream" of the gene sequence. The promoter will be able to promote transcriptional activity using the gene sequence as a template.

A suitable foreign gene sequence is capable of expressing an RNA molecule. This RNA molecule may or may not be translated into a mature protein. A "foreign gene sequence" may alternatively be in the antisense orientation in order to express antisense mRNA. Preferably, the foreign gene sequence encodes a protein.

In one embodiment of the invention, the foreign gene sequence encodes an enzyme catalyzing biosynthesis of a plant hormone, preferably a cytokinin. Most preferably, the enzyme is IPT (isopentenyl transferase).

Standard molecular biological procedures may be used to link the cloned promoter to a protein-coding sequence, such as the IPT sequence. Several genes encoding IPT have been isolated, sequenced and published. The bacterial strains harboring these genes have been deposited with, and are available from, ATCC. With published sequence information, PCR and other gene amplification and recovery techniques may be used to isolate IPT genes. Examples of IPT sequences (also referred to as tmr or tzs) are presented in: Crespi et al., *EMBO J.* 11:795–804 (1992); Goldberg et al., *Nucleic Acids. Res.* 12:4665–4677 (1984); Heide Kamp et al., *Nucleic Acids Res.,* 11:6211–6223 (1983); Strabala et al., *Mol. Gen. Genet.* 216:388–394 (1989).

The genetic construct may be created using either plasmid or viral vectors or other methods known in the art of molecular biology to create a construct capable of being transformed into a plant cell. We describe the creation of a genetic construct suitable to be transformed via the Agrobacterium system. However, there are other means of transformation of plants, and creation of transgenic plants, such as particle bombardment and electroporation, that require many different vector systems. The ability to construct and adopt such vectors to the transformation system to be used is well known to those of skill in the art.

Uses for Senescence-specific Promoters

The availability of effective plant senescence-specific promoters makes possible the creation of transgenic plants with altered senescence characteristics. Genetic constructs can be inserted into plants which become effective only upon plant cells entering senescence. Such senescence-specific expression permits the expression in plants of genes which might be disruptive of plant morphology or productivity if expressed at any other stage of plant development. For example, it now becomes possible to insert a gene encoding a cytokinin biosynthetic enzyme under the control of a senescence-specific promoter without having the tissues of the plant exposed to the excess cytokinin during pre-senescence growth. Then, at the onset of senescence, the senescence-specific promoter activates cytokinin production to alter the progression of senescence in the plant. It has been found, in particular, that the combination of a senescence-specific promoter and a cytokinin-producing gene sequence creates a transgenic plant that, in essence, has a delayed senescence. Such a plant will vegetatively grow longer, producing more flower, seed or fruit, than a corresponding non-transgenic plant. It is anticipated that other coding regions affecting plant maturation and senescence may also be placed behind the senescence-specific promoter and transformed into plants to produce useful transgenic plants with altered senescence.

Another useful application of a senescence-specific promoter is to target the expression of a protein to senescing leaves. For example, if one wished to obtain expression of a protein that is deleterious to plant cells, it may be useful to place the gene encoding the protein under the control of a senescence specific promoter so that the protein will be produced only after the leaf reaches the end of its useful photosynthetic life span.

EXAMPLES

Materials and Methods

Plant materials

Arabidopsis thaliana ecotype Landsberg erecta seed was sterilized in 2.5% sodium hypochlorite for 5 min and rinsed with five changes of sterile water. Sterile seed was imbibed at 4° C. in 1 mM gibberellic acid $A_3$ for 5 hours prior to sowing on a mixture of peat moss, vermiculite and perlite (1:1:1) saturated with Arabidopsis nutrient solution as described in Somerville, et al., *Methods in Chloroplast Molecular Biology*, Elsevier Biomedical Press, New York, N.Y., pp. 129–137, 1982. Plants were grown at 23° C. and 60% relative humidity under 120 $\mu$mol $m^{-2}$ $s^{-1}$ of continuous light from a mixture of cool-white fluorescent (80%) and incandescent (20%) bulbs and sub-irrigated as needed with water. Under these conditions the plants grew vegetatively for about 3 weeks forming 6–7 rosette leaves prior to bolting. Rosette leaves 5 and 6 were harvested at various times after full expansion. All tissues were frozen in liquid $N_2$ immediately after harvest and stored at −80° C.

Quantification of Chlorophyll and Protein

Forty-five $cm^2$ of fresh leaves were soaked at 65° C. for 2 h in ethanol, and the amount of chlorophyll was determined spectrophotometrically (Wintermans, et al., *Biochem. Biophys. Acta.* 109:448–453, 1965). After ethanol incubation the same leaves were used for total protein extraction after they had been briefly dried under vacuum. The leaf residue from forty-five $cm^2$ of leaf material was ground in liquid $N_2$, resuspended in 9 ml of 10 mM $Na_2$Citrate, 1 mM EDTA, 1% SDS, pH 8 and incubated at 70° C. with stirring for 30 min. The soluble and insoluble components were separated by centrifugation. The pelletable fraction was solubilized in 10 ml 1 N NaOH overnight at 30° C. Protein levels in the soluble and pelletable fractions were subsequently quantified according to Lowry, et al., *J. Biol. Chem.* 193:265–275, 1951 combining the modifications of Peterson, *Anal. Biochem.* 83:346–356, 1977 and Larson, et al., *Anal. Biochem.* 155:243–248, 1986. Three replica samples from three independent batches of Arabidopsis were analyzed.

RNA Analysis

Total RNA was extracted as described in Puissant, et al., *BioTechniques* 8:148–149, 1990 and quantitated spectrophotometrically (Sambrook, et al., *Molecular Cloning: A Laboratory Manual*, Cold Spring Harbor Press, N.Y., 1989). For RNA gel blot analyses, RNA samples were electrophoretically fractionated on formaldehyde-agarose gels, transferred to polysulfone membranes (Gelman, Ann Arbor, Mich.), and hybridized to $^{32}$P-labeled probes made by the random prime method (John, et al., *J. Bacteriol.* 170:790–795, 1988). RNA was loaded on a mass basis (5 $\mu$g of RNA per lane) and an area basis (a half leaf equivalent of RNA per lane). The amount of probe hybridized to the RNA was quantitated using a Betagen $\beta$-particle scanner (IntelliGenetics, Inc., Mountain View, Calif.). RNA gel blots prepared from three independent batches of tissue were analyzed for each cDNA clone.

Construction and Screening of cDNA Libraries

Poly (A)+ RNA used for construction of cDNA libraries was isolated as described in Crowell, et al., *Proc. Natl. Acad. Sci. USA* 87:8815–8819, 1990. RNA isolated from S2 and pooled S3 and S4 leaves was used to construct two cDNA libraries. First-strand cDNA was synthesized using oligo $(dT)_{17}$-Xba I as primer with SuperScript™ RNase H⁻ reverse transcriptase and second-strand cDNA was synthesized using *E. coli* DNA Polymerase I, *E. coli* DNA ligase and RNAse H as recommended by the manufacturer (BRL, Gaithersberg, Md.). Double-stranded cDNA was size-fractionated on a BioGel A 0.5m column (BioRad, Richmond, Calif.) to remove cDNAs less than 200 bp in length. EcoR I linker-adapters (Promega, Madison, Wis.) were ligated onto the cDNA then the 5' ends of the cDNA were then phosphorylated with polynucleotide kinase. The cDNA was size fractionated by agarose-gel electrophoresis and cDNAs >500 bp were electroeluted and ligated into pBluescript SKII(+) (Stratagene, La Jolla, Calif.) that had been cut with EcoR I and dephosphorylated. The ligation products were electroporated into *E. coli* strain DH5$\alpha$. Both S2 and S3/4 cDNA libraries contained 1×10⁵ recombinant clones. For library screening, replica filters of the libraries were prepared as described (Sambrook, et al., 1989, supra) and hybridized to cDNA probes made by reverse transcription of poly (A)+ RNA using deoxyadenosine 5-[$\alpha$-32P] triphosphate. For cross-hybridization analysis, probes corresponding to cDNA inserts were prepared using the random prime method and hybridized to dot blots of candidate plasmids (Sambrook, et al. 1989, supra).

Leaf Senescence in *Arabidopsis thaliana* Proceeds Through Defined Phenotypic and Biochemical Changes We divided *Arabidopsis thaliana* rosette leaf senescence into five stages designated S1 through S5 based on phenotypic appearance and measured the amount of RNA, protein, and chlorophyll present at each stage. Leaves at the S1 stage of senescence show the first visible sign of senescence—loss of chlorophyll at the tip of the leaf. As a leaf progresses through senescence, additional loss of chlorophyll occurs. In stage S2, S3, S4, and S5 leaves approximately 25%, 25–50%, 50–75%, and greater than 75% of the leaf area has become yellow. Our visual assessment of these stages corresponds to specific levels of chlorophyll loss. Under our growth conditions, leaves reach stage S1, S2, S3, S4, and S5 at 3, 5, 7, 9, and 10 days after full leaf expansion, respectively.

During senescence, the amount of RNA, protein, and chlorophyll present in a leaf declines. This decrease of RNA and protein has begun by the time chlorophyll loss is first noticeable (stage S1), and continues as the leaf progresses through the senescence program. There is a highly reproducible correlation between the amount of chlorophyll loss and the decline in protein and RNA levels.

Isolation of Senescence-Associated Genes

To identify mRNAs that increase in abundance in Arabidopsis leaves during senescence, we differentially screened a cDNA library constructed from mRNA from senescing leaves. Specifically, two cDNA libraries were constructed from template RNA isolated from S2 leaves and a mixture of S3 and S4 leaves. The S2 and S3/4 cDNA libraries were differentially screened with cDNA probes made by reverse transcribing poly (A)+RNA isolated from non-senescent (NS) leaves and poly (A)+ RNA isolated from S2 or S3/4 leaves, respectively.

Differential screening of the S3/4 cDNA library identified mRNAs that increase in abundance during senescence. From this library, 23 cDNA clones that hybridized more strongly to the S3/4 cDNA probe than the NS cDNA probe were selected for further characterization. We refer to this class as senescence-associated genes (SAGs). Cross-hybridization analyses indicated that this collection comprised six cDNA species. The longest cDNA of each family was used in subsequent analyses. The sizes of the mRNAs that correspond to the SAG cDNAs are presented below in Table 1.

TABLE 1

Approximate mRNA sizes in nucleotides of SAGS

| SAG | Size | SAG | Size |
|-----|------|-----|------|
| 12  | 1360 | 15  | 4560 |
| 13  | 1340 | 16  | 1150 |
| 14  | 1140 | 17  | 800  |

Differential screening of the S2 cDNA library with NS and S2 cDNA probes revealed that the vast majority of the differentially expressed clones hybridized more strongly to the NS cDNA probe than to the S2 cDNA probe. Such cDNA clones correspond to mRNAs that decrease in abundance during senescence. During senescence the photosynthetic output of a leaf and the levels of transcripts encoding proteins required for photosynthesis declines (Hensel, et al., 1993, supra). Therefore, cDNAs corresponding to transcripts encoding photosynthesis-associated proteins are likely to be in this group of clones that decrease in abundance during senescence. Six cDNAs that hybridized more strongly to the NS than the S2 cDNA probe were arbitrarily chosen for further study to provide a contrast to the SAG cDNAs. We designated these clones senescence-down-regulated genes (SDGs) 1 through 6. We wish to emphasize that the SDGs 1–6 correspond to only a small fraction of the cDNAs in the library showing a sharp decline in abundance during senescence.

Gene Expression During Natural Leaf Senescence

The steady-state mRNA levels corresponding to the isolated cDNA clones were investigated temporally throughout leaf senescence. This collection of cDNAs was isolated on the basis of differential expression on a mass basis. Specifically, replica filters of the libraries were screened with an equal mass (measured by dpm) of $^{32}$P-labeled cDNA made by reverse transcription of poly (A)+ RNA isolated from NS or senescing leaves. Since the amount of total RNA present in a leaf decreases during senescence, it is possible that the levels of poly (A)+ mRNA decline correspondingly. If the levels of poly (A)+ mRNA decline during senescence, the differential cDNA screening may have revealed SAG clones corresponding to messages that remain constant during senescence when expression is examined on a per cell basis but increase in abundance when expression is examined as a function of RNA mass. For example, an SAG message that remains at a constant level on a per cell basis would appear to increase in abundance on a mass basis if the levels of the majority of mRNAs were declining.

To address whether SAG mRNA levels increase during senescence, we examined the expression of these messages as a function of both mass and leaf area at each stage of senescence. The steady-state RNA levels corresponding to the SAG genes increase during senescence when examined on both a mass and area basis. The increase based upon leaf area demonstrates that SAG mRNA levels per cell are increasing during senescence. When examined on a mass basis, the levels of all SAG mRNAs are maximal at the later stages of senescence (S3–S5). However, when measured on a leaf area basis, certain SAG mRNAs (e.g., 13 and 15) reproducibly exhibit maximal levels at earlier stages of senescence. SAG12 exhibits one of the highest levels of induction and, within the limits of detection methods, appears to be expressed only during senescence. There is no detectable SAG12 signal in lanes of RNA from non-senescent leaves even with long exposures of the autoradiograph or when measured by a β particle collector. The levels of SAG12 mRNA increase throughout the progression of senescence and reach maximal levels at the last stage of senescence examined.

The steady-state RNA levels corresponding to the six down-regulated genes decrease during senescence when examined as a function of both RNA mass and leaf area. As expected, the reduction is much greater when the expression is examined as a function of area than of mass. As discussed above, the majority of mRNAs in the leaf appear to follow this pattern, including mRNAs corresponding to nuclear-encoded genes involved in photosynthesis such as the chlorophyll a/b binding protein (CAB) and the small subunit of ribulose bisphosphate carboxylase/oxygenase (Rubisco) (Hensel, et al.,1993, supra). We also examined CAB mRNA levels during the stages of senescence that we have defined. We found that CAB mRNA levels drop during leaf senescence at approximately the same rate as the SDGs. However, cross-hybridization analyses indicated that none of the 6 SDG clones were members of the CAB or Rubisco gene families.

Isolation of a Senescence-Specific Promoter

We screened an Arabidopsis genomic library with the SAG12 cDNA for clones that contained the SAG12 promoter region of the SAG12. The library was provided by David Marks of the University of Minnesota.

Figure 2:
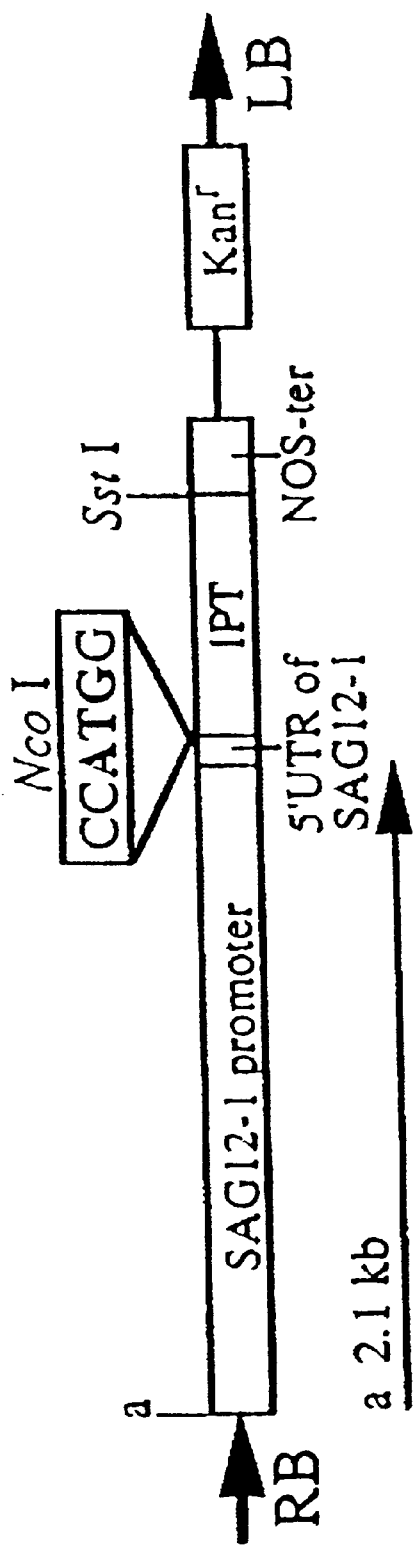
FIG. 2 is a schematic map of SAG12-1 promoter/IPT/NOS-ter construct in a binary vector.

We found that there is one copy of SAG12 in the Arabidopsis genome. FIG. 1 is a diagram of a construct containing 2073 bp of the SAG12-1 promoter and the 5' untranslated region attached to the GUS reporter gene. FIG. 2 is a diagram of the nucleotide sequence of the SAG12-1 promoter linked to the SAG12-1 5' untranslated sequence, the isopentenyl transferase gene and the NOS termination sequence.

The SAG12-1 promoter fragment (from the EcoR V site at—2073 through an Nco I site artificially created at the SAG12-1 start codon by oligo mutagenesis) was cloned into pGEM5Zf(+) (Promega, Madison, Wis.) EcoR V-Nco I sites. This construct was named pSG499. A 2.6 kb Sal I-Sal I fragment containing 1.87 kb GUS and 0.8 kb MAS terminator was cloned into pUC18 Sal I site. The MAS terminator is described in *Plant Mol. Biol.* 15:373–381 (1990). This construct was named pSG468-2. The 2.2 kb SAG12-1 promoter from the Nco I site to the Pst I site in pSG499 was cloned into pSG468-2 at the Nco I-Pst I sites. This construct was named pSG506. The Pst I-Xba I fragment containing SAG12-1 promoter:GUS:MAS-ter was subsequently cloned into a binary vector at the Pst I-Xba I sites, resulting in the construct shown in FIG. 1.

A 1 kb Nco I-Xba I fragment containing 0.7 kb IPT and 0.3 kb NOS terminator sequences (Yi Li, et al., *Dev. Biol.* 153:386–395, 1992) was cloned into pSG506 at the Nco I-Xba I sites to replace GUS:MAS-ter fragment. This new construct was named pSG516. The Spe I-Spe I fragment containing SAG12-1 promoter:IPT:NOS-ter in pSG516 was then cloned into a binary vector at the Xba I site (both Spe I and Xba I have compatible cohesive restriction ends), resulting in the construct shown in FIG. 2.

We mapped the start site of transcription of SAG12-1 (indicated as +1 in FIG. 3) and fused a 2180 bp fragment containing 2073 bp upstream of this start site and the 107 bp SAG12-1 5' untranslated region (UTR) to two genes: the reporter gene beta-glucuronidase (GUS) and isopentenyl transferase (IPT), an enzyme catalyzing the rate-limiting step of cytokinin biosynthesis. The promoter fragment begins at point "a" in FIGS. 1, 2 and 3. SEQ ID NO:1 is the sequence of the SAG12-1 promoter, the IPT gene and the NOS-ter sequence.

These genes were introduced into the genome of both *Arabidopsis thaliana* (Arabidopsis) and *Nicotiana tabacum* (tobacco) by Agrobacterium-mediated transformation (Horsch, et al., *Science* 227:1229–1231, 1985; Valvekens, et al., *Proc. Natl. Acad. Sci. USA* 87:5536–5540, 1988). The resulting plants were fixed and assayed for expression of the GUS gene by calorimetric assay. Analysis of transgene expression demonstrated that the SAG12-1 genomic sequence fused to the reporter gene contains a senescence-specific promoter. In both Arabidopsis and tobacco, the GUS reporter gene was expressed in senescing leaves but was not detectable in leaves prior to senescence.

In transgenic tobacco we have done more extensive analyses and found that the SAG12-1 promoter is also active in flower parts during senescence. This result is not surprising since floral organs are developmentally and evolutionarily related to leaves (i.e., floral organs are thought of as modified leaves).

A 709 bp fragment (602 bp upstream of the start of transcription; point "b" in FIG. 1) fused to the GUS gene confers senescence-specific expression of GUS in transgenic plants, albeit at a lower level than the 2180 bp fragment. Thus, this smaller region contains a regulatory signal sufficient for senescence-specific regulation. SEQ ID NO:2 is the 602 bp upstream from the start of transcription in the SAG12-1 gene and 107 bp of the 5' untranslated region.

Use of the Senescence-Specific Promoter to Delay Senescence

Cytokinins have been shown to be effective at blocking leaf senescence in both detached leaves and leaves undergoing natural senescence on the plant in many species including both monocots and dicots (for review see Noodén, *Senescence and Aging in Plants,* pp. 391–439, 1988 and Van Staden, et al., *Senescence and Aging in Plants,* pp. 281–328, 1988). Moreover, the prevention of senescence by cytokinins results in the maintenance of a photosynthetically active leaf. Several studies have demonstrated that cytokinin treatment stimulates photosynthesis and chloroplast and cytoplasmic protein synthesis while preventing chloroplast breakdown (Van Staden, et al., supra).

While most studies on the effects of cytokinins on senescence have involved application of exogenous cytokinins, there is evidence that endogenously produced cytokinins are a natural regulator of leaf senescence. Noodén, et al. (Noodén, et al., *Plant Physiol.* 93:33–39, 1990) have recently studied cytokinin fluxes in soybean leaves that are undergoing natural senescence on the intact plant. During the later stages of seed development that trigger senescence in soybean, the flux of cytokinins from roots to leaves is drastically reduced. Moreover, removal of seed pods reverses senescence and restores the flux of cytokinins to leaves. Further support is provided by transgenic plant studies. The isopentenyl transferase gene (IPT) from the T-DNA of the *Agrobacterium tumefaciens* Ti plasmid catalyzes the rate-limiting step in the biosynthesis of cytokinins. Transgenic plants that overexpress the IPT gene often exhibit some delay of leaf senescence (Li, et al., *Dev. Biol.* 153:386–395, 1992; Ooms, et al., *Plant Mol. Biol.* 17:727–743, 1991; Smart, et al., *The Plant Cell* 3:647–656, 1991). However, IPT expression in these transgenic plants was not leaf specific and therefore the transgenic plants displayed developmental abnormalities typical of general cytokinin overproduction such as stunted root growth and lack of apical dominance.

The goal was to target cytokinin production to senescing leaves at a level that will block senescence but does not interfere with other aspects of plant development.

Eight transgenic tobacco lines were created using the genetic construct illustrated in FIG. 2. All eight transgenic tobacco lines that expressed the SAG12-1/IPT fusion were perfectly normal phenotypically (i.e., there were no alterations of branching, flower development, root growth, etc.) except that all of the leaves of the transgenic plants retained high levels of chlorophyll throughout flower and seed development. Nontransformed control plants and plants transformed with a construct similar to the SAG12-1/IPT fusion, except that IPT sequences were replaced with the GUS gene, exhibited extensive senescence of lower leaves during flower and seed development. Thus, the goal of altering senescence was achieved without perturbing other aspects of plant development.

The transgenic plants had greatly enhanced yield of biomass and flower and seed production. As shown in Table 2 below, total biomass and flower number were greatly increased in the IPT transgenic plants as compared to transgenic controls that express GUS, although leaf number and flowering time were the same. The seed yield per flower was the same in control and IPT plants; therefore, the seed yield was almost doubled in the IPT transgenic plants. The IPT transgenics were still growing (the controls had stopped growing) when the experiment was terminated due to insect infestation and the actual increase in yield would probably have been greater if the experiment could have been continued. Thus, this system is of potential use to increase yield of both biomass and seed and enhance flower production in ornamental crops.

We have also put the SAG12-IPT construct shown in FIG. 2 into Arabidopsis and shown that it blocks leaf senescence in this species as well.

The SAG12-1/IPT construct was made with an IPT construct provided by Yi Li (Li, et al., *Dev. Biol.* 153:386–395, 1992). The useful feature of this IPT gene was the introduction of an Nco I site at the start of translation. The IPT gene was readily available from our previous work (See, for example, Akiyoshi, et al., *Proc. Natl. Acad. Sci. USA* 81:5994–5998), but we chose Li's construct to save a cloning step. This construct utilizes a "terminator" (a sequence that makes a proper 3' end on the mRNA) from the nopaline synthase gene (NOS) (Bevan, et al., *Nucleic Acids Research* 11:369–385, 1983).

Isolation of SAG13 Promoter

In the mRNA library described above, 23 cDNA clones were identified associated with leaf senescence. The identification of one, SAG12 is described above, and similar methods were used to identify SAG13 and its associated promoter.

The SAG13 clone contained a 1.24-Kb insert. This insert was used to make a probe to screen the Arabidopsis genomic library described above. Two unique genomic clones were found. (i.e., there are two copies of SAG13 in the Arabidopsis genome.) The two clones contained a 3.53 kb EcoRI-SalI fragment that contains the region upstream of the start site of transcription. These DNA fragments were subcloned into pBluescript II SK vector at the EcoRI and SalI sites and were subsequently sequenced. The fragment contained all the SAG13 cDNA sequence and an upstream promoter sequence. The sequence of the SAG13 upstream promoter sequence is set forth in SEQ ID NO:3 below. The transcription start site is at nucleotide 1782 and the translation start site is at nucleotide 1957. The two sequences were identical except at position 1009 where one copy of the gene contains a G residue and the other copy an A residue.

Isolation and Characterization of BnSAG12 Promoters

To identify a potential senescence-specific promoter in Brassica, the radiolabeled Arabidopsis SAG12 gene was used as a probe to screen a genomic library of *Brassica napus,* using low stringency hybridization conditions. Several positive clones were isolated and characterized using hybridization analyses and restriction mapping, which revealed the existence of two distinct genes. These genes were designated BnSAG12-1 and BnSAG12-2. The nucleotide sequences of BnSAG12-1 and BnSAG-12-2 are shown in SEQ ID NO:4 and SEQ ID NO:5, respectively.

To determine whether the two Brassica genes are preferentially expressed during senescence, hybridization studies were conducted using gene-specific probes hybridized under high stringency conditions to blots containing RNA isolated from senescent or nonsenescent Brassica leaves. The results of this experiment revealed that steady-state mRNAs corresponding to BnSAG12-1 increase during senescence of *Brassica napus* leaves by at least about 90 fold, indicating a very strong senescence induction. Steady state mRNAs corresponding to BnSAG12-2 also increase during senescence, but the increase is less dramatic than that with mRNAs corresponding to BnSAG12-1. It would appear that the BnSAG12-1 is a stronger senescence-specific promoter than BnSAG12-2. Thus, both the DNA sequence homology to SAG12 and the senescent-specific pattern of gene expression indicate that both BnSAG12-1 and BnSAG12-2 are SAG12 homologs.

There is a very high degree of sequence homology between bp 1272–1585 of SEQ ID NO:4, bp 2202–2517 of SEQ ID NO:5, and bp 1291–1603 of SEQ ID NO:1. A portion of this conserved sequence corresponding to bp of 1472–1603 of SEQ ID NO:1 and bp 1454–1585 of SEQ ID NO:4 overlaps bp 1–132 of SEQ ID NO:2. Conservation of this sequence is consistent with SEQ ID NO:2 containing a regulatory signal that confers senescence-specific regulation of gene expression, as demonstrated in the examples above.

Construction of genetic constructs comprising a Brassica senescence specific promoter and a GUS reporter gene has been initiated. It is reasonably expected that both the BnSAG12-1 promoter and the BnSAG12-2 promoter, when operably connected to a protein coding sequence not natively connected to the promoter sequence, will direct senescence-specific expression of the protein coding sequence.

TABLE 2

Comparison of some characteristics of SAG12-ipt transgenic and related plants

|  | Wisconsin 38 (Wild-type) | SAG12-gus Plants | SAG12-gus/ SAG12-ipt Plants | SAG12-ipt Plants |
|---|---|---|---|---|
| Chlorophyll content ($\mu$g cm$^{-2}$ leaf #7) | | | | |
| 39-day-old[a] | 19.911 ± 0.642 | 21.627 ± 1.893 | 22.117 ± 1.944 | 25.638 ± 1.877 |
| 69-day-old[b] | 1.239 ± 0.719 | 1.797 ± 1.575 | 16.905 ± 1.551 | 18.527 ± 2.855 |
| Protein content ($\mu$g cm$^{-2}$ leaf #7) | | | | |
| 39-day-old[a] | 52.47 ± 1.75 | 52.27 ± 1.01 | 71.33 ± 7.04 | 71.60 ± 3.86 |
| 69-day-old[b] | 16.00 ± 5.29 | 19.60 ± 10.65 | 54.40 ± 3.49 | 49.60 ± 5.88 |
| Total flower # | 178.3 ± 28.1 | 176.2 ± 51.1 | 318.6 ± 44.2 | 327.5 ± 46.3 |
| Seed yield (g/plant) | 20.436 ± 4.182 | 21.142 ± 3.683 | 30.240 ± 4.037 | 31.154 ± 4.100 |
| Biomass (g/plant)[c] | 107.51 ± 14.41 | 101.64 ± 10.97 | 151.80 ± 20.40 | 150.79 ± 20.15 |
| Plant height (cm)[d] | 176.25 ± 14.27 | 172.54 ± 6.70 | 178.38 ± 10.54 | 180.15 ± 7.91 |
| Leaf # on main stem | 33.3 ± 0.5 | 33.0 ± 0.9 | 33.1 ± 1.0 | 33.5 ± 1.4 |

[a]The #7 leaves of all genotype plants were fully expanded but nonsenescent after 39 days of their emergence.
[b]THe #7 leaves of both wild-type and SAG12-gus plants were completely senesced after 68 days of emergence.
[c]Dry weight of the above soil of the plant excluding seeds.
[d]From the soil surface to the toppest floral stalk.
Sample Sizes: Wisconsin 38: 8 plants; SAG12-gus: 13 plants; SAG12-gus/SAG12-ipt: 8 plants; SAG12-ipt: 13 plants.

We claim:

1. A senescence associated promoter sequence operably connected to a protein-coding DNA sequence not natively connected to the promoter sequence, wherein the senescence associated promoter comprises a DNA sequence having at least about 75% homology to a sequence selected from the group consisting of base pairs 1291–1603 of SEQ ID NO:1, base pairs 1272–1585 of SEQ ID NO:4, and base pairs 2202–2517 of SEQ ID NO:5.

2. The senescence associated promoter sequence of claim 1 which forms part of a genetic construct.

3. A transgenic plant with delayed senescence, the plant comprising in its genome, 5' to 3', a genetic construction comprising a senescence associated promoter and a coding region for an enzyme catalyzing the synthesis of a cytokinin, wherein the senescence associated promoter comprises a DNA sequence having at least about 75% homology to a sequence selected from the group consisting of base pairs 1291–1603 of SEQ ID NO: 1, base pairs 1272–1585 of SEQ ID NO:4, and base pairs 2202–2517 of SEQ ID NO:5.

4. The senescence associated promoter sequence of claim 1 wherein the protein-coding DNA sequence encodes a plant hormone synthesizing enzyme.

5. The senescence associated promoter sequence of claim 4 wherein the protein-encoding DNA sequence encodes an enzyme catalyzing the synthesis of the plant hormone cytokinin.

6. The senescence associated promoter sequence of claim 5 wherein the protein-encoding DNA sequence encodes isopentenyl transferase.

7. The transgenic plant of claim 3 wherein the enzyme is isopentenyl transferase.

\* \* \* \* \*

UNITED STATES PATENT AND TRADEMARK OFFICE
CERTIFICATE OF CORRECTION

PATENT NO. : 6,359,197 B1
DATED : March 19, 2002
INVENTOR(S) : Amasino et al.

It is certified that error appears in the above-identified patent and that said Letters Patent is hereby corrected as shown below:

<u>Column 14,</u>
Table 2, line 2, under "Chlorophyll content ($\mu g\ cm^{-2}$ leaf #7", please delete "69-day-old", and replace with -- 68-day-old --;
Under "Protein content ($\mu g\ cm^{-2}$ leaf #7)", please delete "69-day-old", and replace with -- 68-day-old --.

Signed and Sealed this

Third Day of December, 2002

JAMES E. ROGAN
*Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 3182 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

```
GATATCTCTT TTTATATTCA AACAATAAGT TGAGATATGT TTGAGAAGAG GACAACTATT      60

CTCGTGGAGC ACCGAGTCTG TTTTATATTA GAAACCCGAT TGTTATTTTT AGACTGAGAC     120

AAAAAAGTAA AATCGTTGAT TGTTAAAATT TAAAATTAGT TTCATCACGT TTCGATAAAA     180

AAATGATTAG TTATCATAGC TAATATAGCA TGATTCTAAA TTTGTTTTTT GACACCCTTT     240

TTTTCTCTCT TTGGTGTTTT CTTAACATTA GAAGAACCCA TAACAATGTA CGTTCAAATT     300

AATTAAAAAC AATATTTCCA AGTTTTATAT ACGAAACTTG TTTTTTTAAT GAAAACAGTT     360

GAATAGTTGA TTATGAATTA GTTAGATCAA TACTCAATAT ATGATCAATG ATGTATATAT     420

ATGAACTCAG TTGTTATACA AGAAATGAAA ATGCTATTTA AATACCGATC ATGAAGTGTT     480

AAAAAGTGTC AGAATATGAC ATGAAGCGTT TTGTCCTACC GGGTATCGAG TTATAGGTTT     540

GGATCTCTCA AGAATATTTT GGGCCATATT AGTTATATTT GGGCTTAAGC GTTTTGCAAA     600

GAGACGAGGA AGAAAGATTG GGTCAAGTTA ACAAAACAGA GACACTCGTA TTAGTTGGTA     660

CTTTGGTAGC AAGTCGATTT ATTTGCCAGT AAAAACTTGG TACACAACTG ACAACTCGTA     720

TCGTTATTAG TTTGTACTTG GTACCTTTGG TTAAGAAAAA GTTGATATAG TTAAATCAGT     780

TGTGTTCATG AGGTGATTGT GATTTAATTT GTTGACTAGG GCGATTCCTT CACATCACAA     840

TAACAAAGTT TTATAGATTT TTTTTTATAA CATTTTTGCC ACGCTTCGTA AAGTTTGGTA     900

TTTACACCGC ATTTTTCCCT GTACAAGAAT TCATATATTA TTTATTTATA TACTCCAGTT     960

GACAATTATA AGTTTATAAC GTTTTTACAA TTATTTAAAT ACCATGTGAA GATCCAAGAA    1020

TATGTCTTAC TTCTTCTTTG TGTAAGAAAA CTAACTATAT CACTATAATA AAATAATTCT    1080

AATCATTATA TTTGTAAATA TGCAGTTATT TGTCAATTTT GAATTAGTA TTTTAGACGG     1140

TTATCACTTC AGCCAAATAT GATTTGGATT TAAGTCCAAA ATGCAATTTC GTACGTATCC    1200

CTCTTGTCGT CTAATGATTA TTTCAATATT TCTTATATTA TCCCTAACTA CAGAGCTACA    1260

TTTATATTGT ATTCTAATGA CAGGGAAACT TTCATAGAGA TTCAGATAGA TGAAATTGGT    1320

GGGAAACATC ATTGAACAGG AAACTTTTAG CAAATCATAT CGATTTATCT ACAAAAGAAT    1380

ACTTAGCGTA ATGAAGTTCA CTTGTTGTGA ATGACTATGA TTTGATCAAA TTAGTTAATT    1440

TTGTCGAATC ATTTTTCTTT TGATTTGAT TAAGCTTTTA ACTTGCACGA ATGGTTCTCT     1500

TGTGAATAAA CAGAATCTTT GAATTCAAAC TATTTGATTA GTGAAAAGAC AAAAGAAGAT    1560

TCCTTGTTTT TATGTGATTA GTGATTTTGA TGCATGAAAG GTACCTACGT ACTACAAGAA    1620

AAATAAACAT GTACGTAACT ACGTATCAGC ATGTAAAAGT ATTTTTTTCC AAATAATTTA    1680

TACTCATGAT AGATTTTTTT TTTTTGAAAT GTCAATTAAA AATGCTTTCT TAAATATTAA    1740

TTTTAATTAA TTAAATAAGG AAATATATTT ATGCAAAACA TCATCAACAC ATATCCAACT    1800
```

```
TCGAAAATCT CTATAGTACA CAAGTAGAGA AAATAAATTT TACTAGATAC AAACTTCCTA      1860

ATCATCAATT ATAAATGTTT ACAAAACTAA TTAAACCCAC CACTAAAATT AACTAAAAAT      1920

CCGAGCAAAG TGAGTGAACA AGACTTGATT TCAGGTTGAT GTAGGACTAA AATGGCTACG      1980

TATCAAACAT CAACGATCAT TTAGTTATGT ATGAATGAAT GTAGTCATTA CTTGTAAAAC      2040

AAAAATGCTT TGATTTGGAT CAATCACTTC ATGTGAACAT TAGCAATTAC ATCAACCTTA      2100

TTTTCACTAT AAAACCCCAT CTCAGTACCC TTCTGAAGTA ATCAAATTAA GAGCAAAAGT      2160

CATTTAACTT TCCTAAAACC ATGGACCTGC ATCTAATTTT CGGTCCAACT TGCACAGGAA      2220

AGACGACGAC CGCGATAGCT CTTGCCCAGC AGACAGGGCT TCCAGTCCTT TCGCTTGATC      2280

GGGTCCAATC GTGTCCTCAA CTATCAACCG AAGCGGACG ACCAACAGTG GAAGAACTGA       2340

AAGGAACGAC GCGTCTCTAC CTTGATGATC GGCCTCTGGT GGAGGGTATC ATCGCAGCCA     2400

AGCAAGCTCA TCATAGGCTG ATCGAGGAGG TGTATAATCA TGAGGCCAAC GGCGGGCTTA    2460

TTCTTGAGGG AGGATCCACC TCGTTGCTCA ACTGCATGGC GCGAAACAGC TATTGGAGTG    2520

CAGATTTTCG TTGGCATATT ATTCGCCACA AGTTACCCGA CCAAGAGACC TTCATGAAAG    2580

CGGCCAAGGC CAGAGTTAAG CAGATGTTGC ACCCCGCTGC AGGCCATTCT ATTATTCAAG    2640

AGTTGGTTTA TCTTTGGAAT GAACCTCGGC TGAGGCCCAT TCTGAAAGAG ATCGATGGAT    2700

ATCGATATGC CATGTTGTTT GCTAGCCAGA ACCAGATCAC GGCAGATATG CTATTGCAGC    2760

TTGACGCAAA TATGGAAGGT AAGTTGATTA ATGGATCGC TCAGGAGTAT TTCATCCATG      2820

CGCGCCAACA GGAACAGAAA TTCCCCCAAG TTAACGCAGC CGCTTTCGAC GGATTCGAAG    2880

GTCATCCGTT CGGAATGTAT TAGGTTACGC CAGCCCTGAG CTCGATCGTT CAAACATTTG    2940

GCAATAAAGT TTCTTAAGAT TGAATCCTGT TGCCGGTCTT GCGATGATTA TCATATAATT    3000

TCTGTTGAAT TACGTTAAGC ATGTAATAAT TAACATGTAA TGCATGACGT TATTTATGAG    3060

ATGGGTTTTT ATGATTAGAG TCCCGCAATT ATACATTTAA TACGCGATAG AAAACAAAAT    3120

ATGGCGCGCA AACTGGGATA AATTATCGCG CGCGGTGTCA TCTATGTTAC TAGATCGAAT    3180

TC                                                                   3182

(2) INFORMATION FOR SEQ ID NO:2:

(i) SEQUENCE CHARACTERISTICS:
        (A) LENGTH: 709 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

AAGCTTTTAA CTTGCACGAA TGGTTCTCTT GTGAATAAAC AGAATCTTTG AATTCAAACT        60

ATTTGATTAG TGAAAAGACA AAAGAAGATT CCTTGTTTTT ATGTGATTAG TGATTTTGAT       120

GCATGAAAGG TACCTACGTA CTACAAGAAA AATAAACATG TACGTAACTA CGTATCAGCA       180

TGTAAAAGTA TTTTTTTCCA AATAATTTAT ACTCATGATA GATTTTTTTT TTTTGAAATG       240

TCAATTAAAA ATGCTTTCTT AAATATTAAT TTTAATTAAT TAAATAAGGA AATATATTTA       300

TGCAAAACAT CATCAACACA TATCCAACTT CGAAAATCTC TATAGTACAC AAGTAGAGAA       360

AATAAATTTT ACTAGATACA AACTTCCTAA TCATCAATTA TAAATGTTTA CAAAACTAAT       420

TAAACCCACC ACTAAAATTA ACTAAAAATC CGAGCAAAGT GAGTGAACAA GACTTGATTT       480

CAGGTTGATG TAGGACTAAA ATGGCTACGT ATCAAACATC AACGATCATT TAGTTATGTA       540
```

```
TGAATGAATG TAGTCATTAC TTGTAAAACA AAAATGCTTT GATTTGGATC AATCACTTCA       600

TGTGAACATT AGCAATTACA TCAACCTTAT TTTCACTATA AAACCCCATC TCAGTACCCT       660

TCTGAAGTAA TCAAATTAAG AGCAAAAGTC ATTTAACTTT CCTAAAACC                   709
```

(2) INFORMATION FOR SEQ ID NO:3:

(i) SEQUENCE CHARACTERISTICS:
        (A) LENGTH: 1974 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
GAATTCTCAG TGTTCTCTTA AATCAAATCT CTCACACTAT GAGTATATGA ACAAAATCAT        60

ATACATATCA CAATTCCATT ATGGATATCT CCCAATCTAT CTCTCATACA TGAAAATGTT       120

CTATTTCGAT CTTGTATTTA ATAATGTTAA TACTCTGTTT TAATTTGTGT ATCCTGATTT       180

TTTTTTCTTT TTGAAGTTCA ACAAATATAT CAAAATAACT CAGAACCATT ACTATTTTTT       240

CTTAGTTCAT CAATTCTTTA CTACACATAG AAACGTATTT ATCTTGTTTG ATCTACTTTG       300

ACTCTATATA TGTCATGTGG CATCTCTGGT CATTGCTAGT CACAGGTAAA AGTAAAAATT       360

GATCAAAGAT AAAGAGTCTT TCATGGTAAA AATTCTCTTG TAACTGGTGG AGATAGTAGA       420

TGTCAATTCG TTTGCAATAA CTTACATTTG CAATAACATG TCAGCCATAT TTATTTAAAT       480

TTCCATGCAT TTGATATTAT TTTCTCTCTA ATACATATAT GATGTGTTAC GGTCATTCTA       540

AAAATCCAGT TGACAGCATA ATGAAGCTGG TACACCATAC ATGCACTTGA TTATATATGG       600

ATGTTACTGC CATGATTGAT GTTTTGATGG AATTAGTGTT AAAGGATGGA CCCTCACTAA       660

CGCGGTTGGA AATTATGATC AAACTCTTCA ATGTCACTTA TCAAGAGAGC TAATGACTAG       720

CACGTTTAGT TGTTCTGTTG TTTCTTATGG CTGCTTAATG TCTCCATCAA ATATTTAGAC       780

ATTGTGGCTA GTAAAATGCC ATCTACCTTA ATCCTATATA TAAGTATAAC TAGATAATAA       840

TCCATATTTT TGCTGGGTTT AGTAGCTGAT ACGACGTTTA TGGTTGTTAT TGAGTTTGAA       900

TACAAAATAT AGAGTATTGT TGGAGTTATA TTGATTTTTG TTCATATTAG TTAACAAATA       960

ATAAAAAAAT TAAGAAAGGT TTTTGAAAAT GCATCTTCTA GAATATATRT ATATTCGAAA      1020

AAGTCACATC TTTAATTGAC ATATGTTTTG TTTGTTTGTT TTTTTTTACT GGCCACACAA      1080

ATTGACAACA ATGGTCATGC ATGAAATGAA ATGTTTGTTG TCAATTTTTT TTACTAACTT      1140

GTAATATCAT TATGAAATGA AATAGAAGGT ATATATTACA AAATATTACC TAAAAGTAGA      1200

GCAATCTTAG AAAAAAAAAA AAAAAAAAAA AAAAAGAAA AAGAAAAAGA AACAAGATTA      1260

CAATGCATTT AAAAAGAGAT GGAAAGAATC CGAGCTATCG AATCCAAAGA AGCATCTACT      1320

TCCTCCATCT GTTCTTGTAT CGTCTACCAG AGATGGTGTT CCGGATCTCT CGATCAATAT      1380

TCTTAAAGAT GGTTGTTGGA GGGATCCTTT GGCTATTATG GAGAACATTA TTCGTTTATC      1440

TCCAGATGTG ATAGACAAAG GGCTGTGTGG CCTGTGAGAC CGATGGCCAC TTAATTATTG      1500

GTTTTTTGTC AATGGTTGTG TATGCATAGA AATTCCCACA ACCGTTTGTG GCTTAACACA      1560

ATTTACCAGG GGTTTAAGTG GTTAAATTGA TACATGTAGA TCTAAAGTTT TATGCTAATA      1620

TAAATTAGTT TTAATTATAT AAATTTTAAC TACGCTCATG ACACGTAAAT GGTAGACCAA      1680

TATGTGGTGC TCTATTAACT AAGGGGTGCT TCATTATTAA TTCATAAAGA TTTCTTTACT      1740

ATACAAGACT TGTCAAAAGG AAAAGTAGTA TTTTCGTACT ACGTCTACCC CTCTCACGGA      1800
```

```
TATGTGTGGT CGAGCAGTCA TTATCATAAT GTGGAATTTT GAATTGAGCG AGGTTTCAAA    1860

GTTCAAAACT ATCACAACTA GTCTTGATCA ATTCTATATA AGATCTGTGA TCTTGGTTGA    1920

AGAAAAGAAT CGTCGTAGGT TGATATTTAA CAAGGAATGG CAAAGGAAGG GGGC          1974

(2) INFORMATION FOR SEQ ID NO:4:

(i) SEQUENCE CHARACTERISTICS:
        (A) LENGTH: 5303 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

GTTAGCCACG AAAAGCAGCA TGGTAAAACC GTGGTTCGTA GCCACGTTTA GCAACAGTTT      60

TTTCCAGCCA CGAGGCTATA GCCACGGTAA ATTTCCAATC CATAAGCGTG ACTTATTTTC     120

TTTGTAGCCA CGTTTTTTTT TTCTATAGCC ACTGTATTGT AGTGGCTATG CGGTGAATTT     180

TTACTAGTGA ATAAACATCA AAATACTCAG AATATTATAT TATTATTAAC TGGATACTAG     240

CAAAGAATTT TATATAATAA CAGTATTGAT ATATAGATTT ATTATTAAAA ATAAGTTTAA     300

AATTTATTAT TTGTCACATA CAAGACAAAT GGTATAAACA TATTTAAGTT TTGGCATATA     360

AATTGATAAC AGAAAACCGA ACTGAAACAA CATAAAAAAA CTCAAACCAA ACCAATGTTC     420

ACAAATATTT TAATGGTTCC TATATCGTTG AAACAGAAAA ACCGAAACCT AATCGAAACC     480

AAACCGAGAA TCGAATGGGT ACTAAAATAT TTTAAATACA ATTTATATAC TTTAAAATAT     540

TAATTATCTT TAGTTTTAAG ATTATCAAAT ATTCTAAAAA AAATACTACT TATGACCGAA     600

CAACCCAAAA GATGGATTAC CCTATTACTT TTTATTTGAG ATAGTTAAAA TTATCGTAAT     660

ATCCCGATAG AACTGAATAA AACAAAAAAA TATTCGAAAT ACTTAAATTT ATTTAAGTTA     720

TCTGATATTG TATCCAACAA AATCCAAAAT GTGATTTTTA CACAAACTAT TAAAAATTAT     780

ACAAACGTAA CCGAAAACCG AATTAAACTC AAATTTTACC AGGTTCCTAA CGTTATTATC     840

CGAACCAAAC TAAAAACTAA AATAACCAAA CCGAAACTAA ACATAAATTC ATAAATAACC     900

AAACAGGTCA TACATTTCTT GAACCGAATA AACCAAAATC ACAACCGAAT TGGCACAAAT     960

CGGAAAAAAA AACTAGAACT GAACCTAAAA CCGGACCAAC CAGGGATAAA CATATTAGTG    1020

GACTGACGCA TTAGTAAAAG TTTTAATAAA ATCTAGTAAC GGTTTCAATT AGATAATATT    1080

ACCCGGTGGA CAAAAGTTTG GTCCAGTTTG TGCTTCGGGT TTAATAGTAT TGATGAATTT    1140

CCGTACTCAT CCCGCCAGTG ATCATTCATT TTCTTATATC ATCCCTAGCT GTAACTTTTT    1200

TTTTTTTTTT GACATCCCCT AGCTGTAACT TATAAGCAAT TGTATTGTAT TTTATGGACA    1260

AAATAGAAAA CTTCATAGAA ATTCGAACAG ATGAAATGGG TGAGAAACAT AATTGAAAAG    1320

GAAAGCAAAT CATCATGATT TATCTACAAA AGGATACTTA GCGTAATGAA GTTCACTTGT    1380

TCTGAGTGAT TATGATTCGA TGATTTGATC CAGTTAGTTA ATTTTGTCGA ATCATTTTCT    1440

TCTTTCTTCG TTTAAACATT TAACTTGCAC GAATGGTTCT CTTGTGAATG AACGGAATCT    1500

TTGAATTCAA ATTAATTAAT TAATAAGAAG ACAAAATAAG ATTCCATGTT TTGATAAGAT    1560

TAATGATTTT GATGCATTAA CGGCATATTT GAAACAAATA CATTAATCAG CAAAACTGAG    1620

AATGTTGAAC TACGAAAATT TCAGTTTCTA GTTGAAAAAT AATGATCATA GAGAACATAT    1680

TATAAAACCT CAGAAACGAA CTATGGAGTA GAAATTGGTT AACTGTATTT AGCAAACAAA    1740

AAAGCGTTAA CTGTTACCAT AAACCCATTA TTTTAATTTC TAAATTATGC AAGCTTCCAA    1800
```

```
TCTTAGCCTT TTAAATAAAA AAGACGCTAT GGATTTGGAA TCAGATTGTG AACAACTTGT       1860

GGAACTAATT AACAGAGAAA AAAACTGACC AGCGAATGGC AGTGGAGCTA GATGAGATTA       1920

AAGCCTATGC AACAAGATTT CTGGAGTTTT CGATATTTTT TATCCTTAGA GCTTTAAACG       1980

TCCGTGCAGA TGGCCTTGCT AAAGGAGCTA GATCATGAGT CCTCAGGTTC CCCTCTGTAA       2040

ACGGTTGTGC ACCACGATGG CTAGTACCTA ATACTGGTCA TACGGATGCA TAGGCCTGAG       2100

CGTTCGGGTA CTGGTCATAC GGATGCATAG GCCTGAGCGT TCGGGTACCC GTTGGCGTTC       2160

GGATCGGGTT TTTCGGATTT CAGTTCTTTT TTATAACAGC TCTTAGGTTC CATTCTAGTA       2220

AATTTGCAAG TACGGGTTGG ATTCGGATAT AACACATCGG GTTCGGGTCG GTTTTGTATC       2280

ACATCATAGA ACCCATAAAG TAATCATATA TCATTCGGAT TCAGGTTATA TCGGATCGGT       2340

TCGGATATAC CCGAAATAAA ATCTAAAATT TAAAAATAAA CATAAGAAAT ATATATTTAT       2400

TTATATATAA TTAATTATTT AAGGTAGTTA TTTAAATTTT AAATACTTAT TGTTAGATAA       2460

CATATAAAAT AAATATGAAA TTGAATATTT GAAGTATATA TTCATGTTTC ATATAATTAT       2520

ATTGTATATT ATTTTGGACA TTCGGATCGG TTTCTTCGGA TATTTTTTCG GTTTTTCGGG       2580

TTACCCGTTC GGGTTCGGTT AATAACACTT CGGGTTTAGA TATGTTTTGT ACCACCTTAC       2640

AAGACCCATT CGGATATTTT TTAAATTTCG GACCGGATAC GGATCGGGTT TTTTGGTTCG       2700

GGTTCGGTTC GGATTCGGG TTACGGATAT TATGCTGAGG CCTACGGATG CAAACCAGTA       2760

AGCTGGATTG ATTTTTTCCA TGTCAAAAAA AAGACAATTG CTAGTTTCCA ACAAATATGT       2820

TTTCTGATGG TATTTTCAGG TTTTTGTAAC AAATATAATT TTTAAATGTT TCCTTAATAT       2880

TTGATTTTCA ATTTTTATAT CAATAAATAT ATTTGTCCAA ATACCAATCA GTATCCAAGT       2940

TCGAGTATCG TTAAGCCTTG GGAGATTAAA GTCTAATAGG TTCGAGCCAT GATGAGTTCT       3000

AGTTATCTAC ATAGATGTAT ATATAAGATG ATCATTACTT GTAAACTAAA AATACTTTGT       3060

CATAATCACT TCATAGGAAC ATTACCAATA GTATCACACT TTTTGCACTA TAAAACCCCA       3120

CTGCAAAACC CTTTTGGAGT AATCAAACTA GTATCTAAAT CCTTCAACTT TTCTAAAACA       3180

ATGGCTTTAG AACACATCAA AATCTTTCTC ATTGTCTCTC TAGTTTCATC ATTCTGTTTC       3240

TCGACCACTC TTTCTCGTCT TCTCGACGAT GAACTCATCA TGCAAAAGAA GCACGACGAG       3300

TGGATGGCCG AACATGGACG TACTTACGCA GATATGAATG AGAAAAACAA TCGCTACGTT       3360

GTGTTCAAAC GCAACGTGGA ACGCATTGAA CGCTTAAACA ACGTTCCCGC CGGGAGAACG       3420

TTTAAACTCG CGGTAAACCA GTTTGCTGAT TTAACCAACG ACGAGTTCCG TTTTATGTAC       3480

ACTGGTTACA AAGGAGACTT TGTTTTGTTT AGCCAAAGTC AAACAAAATC CACGTCGTTT       3540

AGGTACCAAA ACGTTTTTTT TGGTGCTTTG CCCATTGCTG TTGATTGGAG GAAGAAAGGA       3600

GCTGTGACTC CTATCAAGAA TCAAGGCAGT TGTGGTAAAT ATAATTCATA ATCTTTATTC       3660

ATGTATATAA ATTAAAGAAC TAAAGCAAGT TAAGATTTGA ACCGTTTTTG TTGTTGAAAC       3720

TGAAAGAAG TTGGTTTCTT TGTCCCAAAC GATTTGATCA CTTAATTTTG TACCGAATAT       3780

AAACAAAATA CAACCAAACA ATAACAAGTT CATTTTTAGT TATATGTATA TACAAAATAT       3840

AAATAGATTT CTGTATACTA AATTAAGAGA GAAATTATT CTTATATATA TTTTAAGTAG       3900

CTTCTATTCC AAAACCGGAG CTAATATGAT TGAGGATTTT AAACCGAACT TAAAATTTCC       3960

AGCTATGAAT GTTCAAAACC GAAAAAAACA AGAATATATA ACCCAACCAG ATCAAATAAC       4020

CATCCCTAAG ATAATTTTGC ATGGGTGGTG AAACTAATTA ACGAGGGAGT GTACGTGTAG       4080

GATGTTGTTG GGCGTTTTCA GCGGTTGCGG CTATAGAAGG AGCAACGCAG ATAAAGAAAG       4140
```

-continued

```
GGAAACTTAT TTCTTTGTCA GAACAACAGC TTGTAGACTG CGACACAAAC GATTTTGGCT      4200

GCAGCGGCGG TCTAATGGAT ACTGCGTTTG AGCACATAAT GGCCACTGGC GGATTAACCA      4260

CTGAATCAAA TTATCCTTAT AAAGGCGAAG ACGCCAATTG CAAGATCAAG AGCACTAAAC      4320

CGTCAGCAGC TTCTATCACA GGTTTCACTT TTATTCTCTG ATAAAAGTCA TACAAAAGAT      4380

TTGAAATGCA CATAATAAAC CCAAAGTTAA TCGGACAAAC TCTAAATAAT TAAATATAAG      4440

AAAAAAATTG TTTATAGAGA ATACCAAACC AAACCGAATA TAACAAATCA TCATACATAA      4500

CCACACCAAC TTTCAAAATT CGATCATAAT TCTCACAACT GAGTATACAA AACAAGATCA      4560

GTCCCTGAGA TTTTGGGAGT TGCCTATATA ATTGGGTACG AATTCTAATC ATTTGTTCAC      4620

GAATAATAGG CTATGAGGAT GTCCCTGTTA ACGACGAGAA TGCTCTAATG AAGGCAGTGG      4680

CACACCAACC GGTTAGCGTT GGAATAGAAG GAGGTGGTTT TGATTTCCAA TTCTACTCGT      4740

CCGGTGTGTT TACCGGAGAG TGCACAACGT ATCTTGATCA CGCGGTGACT GCCGTAGGAT      4800

ACAGCCAATC TTCCGCCGGA TCAAAGTATT GGATCATCAA AAACTCATGG GGAACAAAAT      4860

GGGGAGAAGG TGGATACATG AGGATTAAAA AAGATATCAA GGATAAAGAA GGATTATGTG      4920

GTCTTGCCAT GAAGGCTTCT TACCCAACTA TATGAAAAAC CGGTTCAATA CCCGGTCAAG      4980

TTTAAAATGT GTATATGTGT GGGGTTTTAT GTCTTAAAAT GGTGATATGA ATAGTTTGTA      5040

TGGGTGTCAC AAAAAAAAAA AAGTTTGTAT GGTTATTATA ATTAAAAACT GTTGCATGTA      5100

ATCTGTGAAA AAAATAAGGA TGCAAAAAAT TTAATAAGTT CAGATTGTTA ATTTCAAATT      5160

TAGTCACGTA AGTTCGATAT CAATGAATCT TGACAATAAT AGCTAGGTGC AACTTCAAAC      5220

AAGTACGCAA AATAATATGA AAACGGATGA TAAGTAAAGA TTTCATTTAA TGCCTAAAGC      5280

AAAATAGGAT GTGAAAATGG ATG                                             5303
```

(2) INFORMATION FOR SEQ ID NO:5:

(i) SEQUENCE CHARACTERISTICS:
        (A) LENGTH: 5185 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
TCCGGCGAAG TTCAGCCGTT TCGCAACAGC TCCGGTTGAG ATGATGACGG AATTGGTGCT       60

TCGGCGAGCA CCGTTCTTGA ATCGGTGAAG AGCTTGAACG GCCTCGAGGA GAAATCAACC      120

TTGGTGACCT CTCCGTGAAG ATCTCGGTGC CAAACCTCTC TGATGATTGC TTCCGGAACT      180

TGTCGACGAT GTCGATGCCA AGGATGCCTA AGGGGAAGTT GGCACTACAA AAAAAAGTCT      240

ACATTGATAG CACATTGTTA CAATACGTTT TACTAAACAA AACTGCTATC GTAGATGATT      300

TAAAAAATTT CGTATCATAT AATAGCATTA GATAAATGCT ATAAAAGAGT TTTAGTAAGC      360

AGGAACTTAA AATTAGATAT TCCGCTAAAT ACTTTGTGAA AATCTCATCA CTAATCAATT      420

TTCCTCTCTT TAATTCTCAT TTTTCCCTCT CTTAAAAAGT AACCACTAAG GTGCAAGTGC      480

GAGGATCCAC TTTCTTTTAA CTACAACCAT TGATTAAAAT AAATCTAATG GCCCAAAATG      540

AACAAAGTGA AAAATGTGTT CTTCCTCTAT CTCCTACCTT TCCTTTCGTA TTCTCTATCT      600

TTTTTTTTC TTTTGAACAA AGGCTTAACT CTATCTCTTT TCTTATCTCA TGTTCTTCAT      660

TCTTAAACAA AATTACCCCA TAAACGAAAT CTGTCACAGC CACCACCATC ACCATAATCT      720

CTGTCTCCTC GTTCTCTACC TCCGCTAACG AAGCTGTCTC AGCCACCATC ACCATAAACC      780
```

-continued

```
TCCGCCGCTG CCACCATCTT CTTAATCTCC ACCTCCTCGT TATCGTTCTC CGCTAATGAA      840

CTCTGTTTCA ACCATCACCA CGAAATATGT CTCAACCACT CTTTTATCTA TTCTCTTATC      900

AAAACTTATT CTTGTCCAGA TGCAGATTCA TGAAGAAGAT GGAGTTTTCT CCACCATCGA      960

TTCGAGATCT GATGCGAGTA ATGAGAGATT GGCTGGAAGC GGAGACATGA TGAAGCTACG     1020

GTGGAGGCGG TGAAGCCGAA GGAGTAGTAA CCGAAGTCGG GCTTAGAGAG GAAGAAGACG     1080

ACGAAATTCA TGGTGGTGGT TAGCTGACCG CCGGGAGGCG AGGCTTGAGC TCCTGGCCCA     1140

ATGCATCGAT TCTTCAGGAT TAGGCCCAGA CACGCGATTA CACAGTCCAA GCCCACACCA     1200

GAGTTAATGA AACGGTGAGT CTCATGTTCA GGACATGTGG CGCGATTGTA TGAAGCGAGT     1260

TTCCAGGCTG GATCCGACGT GGCGCAACAG GAGGGACACA AACATTTTTT TATATATATA     1320

GATTTGGTTT AAGCTTCATA AATTTCATGG GCTTTAAAAT ACACATCTTG CTATTGGATA     1380

CGCATCTACA GTGAGGTTCT ATCCATTGAA ATTTTAATAT ATAACATATA TTAATATTTA     1440

ATTTTGGGCC TTTAATTTTA TAAAAAACCC AACCCAAATG ATTTTAAAAA TTTAGATTGA     1500

GTTTTCCATA AAATTAAGAA TTCCATAGTT AAATATTATT ATAAATATAT TTGTATGTAT     1560

GTTTAGAACT CTAACGGGTA TAACCTTCCC CATTAGAGGT GCTCTTAACA TATCTCCAAA     1620

ATGATTAAGT GGAAGGTGTT CAGCCCAAAG CTTTAATTTT GGAATGTTCA CTTATCACTA     1680

TTCTTATTGC CGTTACAATT TGACTTCTAA TCCTCCTTAG CAAGTAAATT ATGTTGATTT     1740

ATAGAACATT TTTTTATGCT GGCATGTAGT TCAAATTTTC CTGTTGAAAG TTAGGACAAA     1800

GTTTGATACA TTTCATGACA TCGAAACAGT TAAGTTTAGT TGATTTCATT TTAGAAACAA     1860

CAATTTAAAT CATTTCTTGT ATGTACAAAT TACGAATAAG TTTTGATGAT AGTTAAATTT     1920

TGTCTGATAA TAATTATATT ACTCAGTAAA ACATTTTTTT TAATTTATGT ACATATGTAT     1980

GATGTATCTT TTTATTATTA ATGATAGTTC CACATATGTA TCTTTTTTTA TTTAGTCGTT     2040

TAGACATCGT TCTCACTTCG GCCAATTATA ATATGGATTT ATGTCCAAAA ATGACATTCC     2100

GTAAACATCT TTGTTAGCGC CCGATTTATA ATTTTACTTC TATTGTCCCT AACTAAAACT     2160

TATTACCACT TATATTGTAT TTTATAGACA AAATGGAAAA GTTCATAGAA ATTCGAATAG     2220

ATGAAATTGG TGGGAACATC ATCGAACAGG AAACTTTTGG GCAAATGGTT TAGATTTATC     2280

TACAGATACG TACTACTTAG TGCAATGAAG TTCACTTTTG TTGTGAGTGA CTATGATTCG     2340

AAATTAATTT GTCGAATCTT TTTTCCCTTT GTTTTAAGCT TTTAACTTGC ACGGATGGTT     2400

CTCTTATGAA TAAAGGAAAT CTAATTCTTG AATTTAAATT TAATTAATTA ATTAATTAAA     2460

AGACAAAAGA AGATTCCATG TTTTGATGAG ATTAATAATT TTGATGCATC AGAAGTATAT     2520

TTAACATGTG AAAACCAAAT GAATTACGTT TTTTCATGCA TACATTGAGT AGCTGAAATT     2580

GGTTAGTTTC AAACAAATAT GTTTTCAGAT TATATTTGCA GTTTTTTTGT TCCACATGTC     2640

ATTCTTAATT TTGAATTTCA GTTTCAAATA AATAAATATA TTTGTCCAAA ACAAAAACCA     2700

GTTTCGATTT CAAAGTTCGA ATATCATAAG CCTAGAGAGA TTAAAGTCTA ATAAGTTCAA     2760

CTTTCTAATT ATTAAATGTA TTTGTTTACA AACTTAAACC GCAGCTGTAA CGAAAAATGC     2820

AGCCAAACTG AAAGTGAAGA GGATGAGTGT ATCTCAGTTT GATCTTTGAT GTAGAAAAAA     2880

TACTTAACAA CCATAAATAA ACTTAACAAG CCATGCATGA TCGATCTGGT TATGTATATA     2940

TGGATCATGG ATGTATAAGA TGATCATTAC GTGTAAACTT AAAATACTTT GTCCTAATCA     3000

CTTCATGGGT ATATTACCAA TAACATCAAA CCTTTTCACT ATAAAACCCC ACTTCCAAAA     3060

CCTTTTGGAG TAATCAAATT AGTATCAATA TCCTTCAACT TTTCTAAACC AAATGGCTTT     3120

AACACAGATC CAAATCTTTC TCATTGTCTC TCTAGTCTCA TCATTCAGTT TATCGATCAC     3180
```

```
                                                        -continued

TCTTTCTCGT CCATTACTCG ATGAAGTCGC CATGCAAAAG AGACATGCCG AGTGGATGAC    3240

CGAACACGGC CGTGTTTACG CAGATGCGAA CGAGAAAAAC AACCGCTACG CTGTTTTCAA    3300

ACGCAACGTG GAACGCATTG AACGCTTAAA TGACGTTCAA TCCGGACTAA CGTTTAAACT    3360

CGCGGTGAAC CAGTTTGCTG ATCTAACCAA CGAAGAATTC CGTTCTATGT ACACTGGTTT    3420

CAAAGGAAAC TCTGTGTTGT CTAGTCGAAC TAAACCAACG TCGTTTAGGT ACCAAAACGT    3480

TTCTTCTGAT GCGTTGCCGG TTTCTGTTGA TTGGAGGAAG AAAGGAGCTG TGACTCCTAT    3540

CAAGGATCAA GGCTTATGCG GTAATATAAT GCCAAAGCTT TATTCGTTTG TATATGTATA    3600

AACTAAACCA AGCTAAATTT TGAACCGGGA TAATCGAACA ATTTGGTTTC CTTATCCCGA    3660

ACGATTTTAT CTCTTAATAG TTAATATATA CAGAATATAA CCCGAACAAA GACCGAAGTC    3720

TAGTGTAACT AAACCAATCC AAATTAATTA CAAGTATCTG TTTAGTTATA CTGTATACAA    3780

AATGAAATAT TTATATTAAG TTCTGATGGA AATTTTTTTT GAATATTTTA GTAGTTTCTG    3840

CTCCAAAACC GAGACTGGTT TGAACCGATA ATTTTAAAAG GAACTGTAGA ATTCCGGTTA    3900

TGGATGCTCA AACCCAAAGA GTTAGTTGCT TGGATAGTGA AACTAACGAG TGAATGTTTT    3960

GCGTAGGATC TTGTTGGGCG TTTTCAGCTG TTGCGGCTAT AGAAGGAGTA GCACAGATAA    4020

AGAAAGGGAA ACTCATTTCT TTGTCTGAAC AAGAGCTTGT CGACTGCGAC ACAAACGATG    4080

GTGGCTGCAT GGGCGGTTTG ATGGATACAG CGTTTAACTA CACAATAACT ATTGGCGGCT    4140

TAACCTCTGA ATCAAATTAT CCTTATAAAA GCACAAACGG CACTTGCAAC TTCAATAAAA    4200

CTAAACAGAT AGCAACTTCT ATCAAAGGTT TCCCTTTAAT AATTCCCTCA TAAAAGTCGT    4260

AGAAAAAGAT TCATATAATA ATCCGAAAAG TTAACCGAAT AAACAAAAAA CTAATTACAA    4320

AAATCAAAAT AATAAAATAA TAAAATTGAC GAAACATAAC TAAACAAACC AATCGAAATA    4380

CGCAAATGTC TAAATACTAA TGCTCATGGT TTGGTTTTTG AAATGAGAAG ATACTAGTTC    4440

TCATGCTTTG AAATTATATC TCTTCTACAC ATATCATAGG TTTTGAGGAT GTCCCGGCTA    4500

ACGATGAGAA AGCCCTAATG AAGGCAGTGG CACACCACCC GGTTAGCATT GGAATAGCGG    4560

GAGGAGATAT TGGTTTCCAA TTCTATTCGT CCGGTGTGTT CAGCGGAGAA TGCACAACTC    4620

ATCTTGATCA CGGGGTAACT GCGGTTGGAT ACGGCCGATC TAAAAACGGA TTAAAGTACT    4680

GGATCCTCAA GAATTCATGG GGACCAAAAT GGGGAGAACG TGGATACATG AGGATCAAAA    4740

AAGATATCAA GCCTAAACAC GGACAATGTG GTCTTGCCAT GAATGCTTCT TACCCAACTA    4800

TGTGAAAAAA TCGGTTCAAT ATCCGGTTAA GCTTTAGAAT AAATGTGTGT GTTGGTTATA    4860

ATTTAAGACT CTGTTGCATG TAATTTGTGA AATGGTAAGT TTATGTGATG CAAAAGATTT    4920

GATACTTTGA GTAAAAGTTG AGAACTTCAT TGTATAACTG ATATGGGGTT TGCTATCATA    4980

ATGAAATCAG ATTCTCTTAT CATAAGCTTC AATATCTTTT TTCTTGGATT GGAAACTGCA    5040

GGTTACTATG CCCCATGTTC TCATCCACAA GTCTCAAACC ATTTGACTCT TCTTTCAGAC    5100

TCATTGCCTA CATCAGATGA TGAACAGTCA TCAACCGAGA GTACTAGTCA TGGAAATAGG    5160

AACAAGTGTC CTGTTCCAAT ACGGT                                         5185
```